United States Patent
Downs et al.

(10) Patent No.: US 7,297,514 B2
(45) Date of Patent: Nov. 20, 2007

(54) METHOD FOR PREVENTING SUPEROXIDE DAMAGE TO CELLS AND OXYGEN-LABILE PROTEINS

(75) Inventors: Diana Downs, Madison, WI (US); Jeff A. Gralnick, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/955,502

(22) Filed: Sep. 18, 2001

(65) Prior Publication Data

US 2002/0072118 A1   Jun. 13, 2002

Related U.S. Application Data

(60) Provisional application No. 60/234,588, filed on Sep. 22, 2000.

(51) Int. Cl.
*C12P 21/04* (2006.01)
*C12P 21/06* (2006.01)

(52) U.S. Cl. .................. 435/69.1; 435/69.2; 435/71.1; 435/71.2

(58) Field of Classification Search ............... 435/69.1, 435/6
See application file for complete search history.

(56) References Cited

OTHER PUBLICATIONS

Portray et al., J. Biol. Chem. 274(21):15041-15045, 1999.*
Kelner et al. J. Biol. Chem. 275(1) :580-584, 2000.*
Ben-Amor Plant. Cell and Enviroment, 22(12) 1579-1586, 1997.*
Gralnick et al. Abstracts for the General Meeting of the American Society for Microbiology 100 p. 441, 2000.*
Dianzzole et al., J. Bacteriology 178(23) 6736-6742, 1996.*
On-Line Medical Dictionary, definition of Eubacteriales, Eubacteria, eubacterium.*
Gifford et al (Journal of Bacteriology, 181(14):4223-4236, Jul. 1999).*
Attwood et al (Science, 290:471-473, Oct. 20, 2000).*
Pomposiello P.J. et al., J. Bact. 185:6624-6632, SoxRS-Regulated Expression and Genetic Analysis of the yggX Gene of *Escherichia coli*; Nov. 2003.
Osborne, MJ et al., Protein Sci 2005 14:1673-1678; The solution structure of the oxidative stress-related protein YggX from *Escherichia coli*.
J. Gralnick and D. Downs, "Protection from Superoxide Damage Associated with an Increased Level of the YggX Protein in *Salmonella enterica*," PNAS 98(14):8030-8035, 2001.

* cited by examiner

*Primary Examiner*—Patricia A. Duffy
(74) *Attorney, Agent, or Firm*—Quarles & Brady LLP

(57) ABSTRACT

A method of reducing superoxide damage to a cell is disclosed. In one embodiment, this method comprises the step of engineering the cell to produce more than a native amount of the YggX protein or its homolog, wherein the cells are rendered more resistant to superoxide damage.

2 Claims, 8 Drawing Sheets

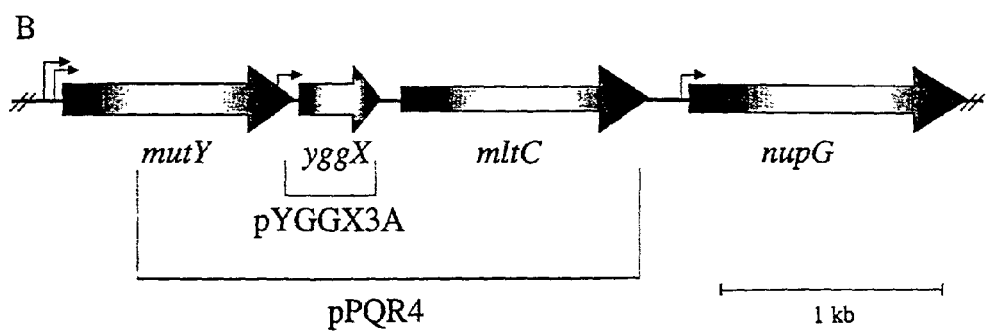
Fig. 1. Physical parameters of yggX and its gene product. (A) Alignment of YggX homologs. (B) Operon structure of mutY/yggX in E. coli and S. enterica LT2. Promoters were mapped by Gifford and Wallace in E. coli (43).

| SEQ ID NO | Organism | Sequence |
|---|---|---|
| SEQ ID NO:2 | Bpertussis | 1 MSRIVNGVKLKREAEGLDFPPYGELGTRIVQQISKEAEEAKQIQTRLVNENRLNLADA |
| SEQ ID NO:3 | Bparapert | 1 MSRIVNGVKLKREAEGLDFPPYGELGTRIVQQISKEAEEAKQIQTRLVNENRLNLADA |
| SEQ ID NO:4 | Bbronchi | 1 MSRIVNGVKLKREAEGLDFPPYGELGTRIVQQISKEAEEAKQIQTRLVNENRLNLADA |
| SEQ ID NO:5 | A.actin | 1 MARMVFGERLKQEAEGLDFQLYGELGKRIEDSISKQAWGEAMKKQTMLVNEKKLNMMNA |
| SEQ ID NO:6 | Pmultocida | 1 MARTVFGEYLKQESEGLDFQLYGELGKRIEDSISKQAWREAMKKQTMLVNEKKLNMMNA |
| SEQ ID NO:7 | Hinfluenzae | 1 MARTVFGEYLKKEAEGLDFQLYGELGKRIEDSVSKQAWGERIKKQTMLVNEKKLNMMNA |
| SEQ ID NO:8 | Hducreyi | 1 MARMVFGEYLKKEAEGLDFQLYGELGKRIENSISKQAAAEAIKKQTMLVNEKKLNMMNP |
| SEQ ID NO:9 | Sputrefasciens | 1 MARTVNGVHLNKEADGLDFQLYGDLGKRIEDNISKEAVGLAQKKQTMLINEKKLNMMNV |
| SEQ ID NO:10 | Vcholerae | 1 MARTVFGTRLQKEADGLDFQLYGELGKRIEDNICKEAVAQAQTKQTMLVNEKKLNMMDP |
| SEQ ID NO:11 | Ecoli | 1 MSETIFGTFLQREAEGQDFQLYGELGKRIVNEISKEAVAQAQHKQTMLINEKKLNMMNA |
| SEQ ID NO:12 | O157_H7EDL933 | 1 MSETIFGTFLQREAEGQDFQLYGELGKRIVNEISKEAVAQAQHKQTMLINEKKLNMMNA |
| SEQ ID NO:13 | O157_H7 | 1 MSETIFGTFLQREAEGQDFQLYGELGKRIVNEISKEAVAQAQHKQTMLINEKKLNMMNA |
| SEQ ID NO:14 | Spara | 1 MSETIFGTYLQRDAEGQDFQLYGELGKRIVNEISKDAVAQAQHKQTMLINEKKLNMMNA |
| SEQ ID NO:15 | Senteritidis | 1 MSETIFGTYLQRDAEGQDFQLYGELGKRIVNEISKDAVAQAQHKQTMLINEKKLNMMNA |
| SEQ ID NO:16 | Sdublin | 1 MSETIFGTYLQRDAEGQDFQLYGELGKRIVNEISKDAVAQAQHKQTMLINEKKLNMMNA |
| SEQ ID NO:17 | StyphiCT18 | 1 MSETIFGTYLQRDAEGQDFQLYGELGKRIVNEISKDAVAQAQHKQTMLINEKKLNMMNA |
| SEQ ID NO:18 | Styphimurium | 1 MSETIFGTYLQRDAEGQDFQLYGELGKRIVNEISKDAVAQAQHKQTMLINEKKLNMMNA |
| SEQ ID NO:19 | Kpneumo | 1 MSETIFGTFLQREADGQDFQLYGELGKRIVNEISKEAVAQAQHKQTMLINEKKLSMMNP |
| SEQ ID NO:20 | Ypesits | 1 MSETIFGTFLKKDAERQDFQLYGEIGKRIVNEISKEEVSQAITKQTMLINEKKLSMMNI |
| SEQ ID NO:21 | Buchnera | 1 MNFIIFGTFFKKKSEGQDFQSYGKLGKKIVDQISKKAVEKAIEKQIILINEENLNMFNL |
| SEQ ID NO:22 | Xfastidiosa | 1 MQRILFGEYEQRDTEGLDFVPYGELGQKIBACIGKVGAAALVHQTMLINENRLSPRNP |
| SEQ ID NO:23 | Psyring | 1 MTRTVMCRKYKEELPGLERAPYGAKGEDIVNHVSQKEAADAQKHQTLLLINERRLNMMNA |
| SEQ ID NO:24 | Pputida | 1 MTRTVMCRKYQEELPGLERPPYGAKGQDIVEHISQKEVADVQKHQTMLINERRLNMMNA |
| SEQ ID NO:25 | Paeruginosa | 1 MSRTVMCRKYHEELPGLDRPPYGAKGEDIVNNESRKEVDEAQKHQTMLINERRLNMMNA |
| SEQ ID NO:26 | Ngonorrhoeae | 1 MARMVFGVKLNKEAEGMKFPPLENELGKRIEENVSQEAAAATRHQTMLINENRLSLADP |
| SEQ ID NO:27 | NmeningitB | 1 MARMVFGVKLNKEAEGMKFPPLENELGKRIEENVSQEAAAATRHQTMLINENRLSLADP |
| SEQ ID NO:28 | NmeningitA | 1 MARMVFGVKLNKEAEGMKFPPLENELGKRIEENVSQEAAAATRHQTMLINENRLSLADP |
| SEQ ID NO:29 | Bmallei | 1 MARMIHQAKLGKEAEGLDFPPLGELGKRIVESVSKQAVQDALKQQTMLINENRLNMADP |
| SEQ ID NO:30 | Bpseudomallei | 1 MARMIHQAKLGKEAEGLDFPPLGELGKRIVESVSKQAVQDALKQQTMLINENRLNMADP |
| SEQ ID NO:31 | Tferrooxidans | 1 MSPMVQGVKLGHEAEGLDRPPYGALGARIVQEVSKEEVQGALKHQTMLINEYRLSPIDP |
| SEQ ID NO:32 | Mcapsulatus | 1 MARRIQAKLGIEADGLDAPPFGPQGQRIEEHVSKEEVQDALKLQTMLINEHRITPFEA |
| SEQ ID NO:33 | Cburneti | 1 MTERIIGQKLGKEADALNYSPYGELGERIVNHISEQAVQAALSHQTMLINEYRLSLIDP |

Fig. 1A

| SEQ ID NO | Organism | | Sequence |
|---|---|---|---|
| SEQ ID NO:2 | Bpertussis | 61 | RARKYLQQQMERELFEDGTVEAQGYVP---- |
| SEQ ID NO:3 | Bparapert | 61 | RARKYLQQQMERELFEDGTVEAQGYVP---- |
| SEQ ID NO:4 | Bbronchi | 61 | RARKYLQQQMERELFEDGTVEAQGVP----- |
| SEQ ID NO:5 | A.actin | 61 | EHRKLIEQEMVNELFEGKDVHIEGYTPPEAK |
| SEQ ID NO:6 | Pmultocida | 61 | DHRQLIEQEMVNELFEGKDVHIEGYVP---- |
| SEQ ID NO:7 | Hinfluenzae | 61 | EHRKLIEQEMVNELFEGKDVHIEGYVP---- |
| SEQ ID NO:8 | Hducreyi | 61 | EHRQLIEAEMVNELFEGKDVHIDGYVP---- |
| SEQ ID NO:9 | Sputrefasciens | 61 | DDRKFIEAQMTSELFEGKDVEIEGFVPE--- |
| SEQ ID NO:10 | Vcholerae | 61 | EHRKLIEQEMVNELFEGKEVHIEGYTPPAK- |
| SEQ ID NO:11 | Ecoli | 61 | EHRKLIEQEMVNELFEGKEVHIEGYTPEDKK |
| SEQ ID NO:12 | O157_H7EDL933 | 61 | EHRKLIEQEMVNELFEGKEVHIEGYTPEDKK |
| SEQ ID NO:13 | O157_H7 | 61 | EHRKLIEQEMVNELFEGKEVHIEGYTPEDKK |
| SEQ ID NO:14 | Spara | 61 | EHRKLIEQEMVSELFEGKDVHIEGYTPEDKK |
| SEQ ID NO:15 | Senteritidis | 61 | EHRKLIEQEMVSELFEGKDVHIEGYTPE--- |
| SEQ ID NO:16 | Sdublin | 61 | EHRKLIEQEMVSELFEGKDVHIEGYTPEDKK |
| SEQ ID NO:17 | StyphiCT18 | 61 | EHRKLIEQEMVSELFEGKDVHIEGYTPEDKK |
| SEQ ID NO:18 | Styphimurium | 61 | EHRKLIEQEMVSELFEGKDVHIEGYPTEDKK |
| SEQ ID NO:19 | Kpneumo | 61 | EHRKLIEQEMVQELFEGK------------- |
| SEQ ID NO:20 | Ypesits | 61 | EDRKLIEQEMVNELFEGQDVHIAGYTPPSK- |
| SEQ ID NO:21 | Buchnera | 61 | EHRKKIEKYMKLELFK--------------- |
| SEQ ID NO:22 | Xfastidiosa | 61 | SHRAFLEEELNKELFERRVAKPEGYIEPD-- |
| SEQ ID NO:23 | Psyring | 61 | EDRKFLQTEMDKELSGEEYAQAEGYVPPEK- |
| SEQ ID NO:24 | Pputida | 61 | EDRKFLQAEMDKEFAGEEYAQAEGYVP---- |
| SEQ ID NO:25 | Paeruginosa | 61 | EDRKFLQQEMDKELSGEDYAKADGYVP---- |
| SEQ ID NO:26 | Ngonorrhoeae | 61 | RAREYLAQQMEQYFFGDADAVQGYVPQ--- |
| SEQ ID NO:27 | NmeningitB | 61 | RAREYLAQQMEQYFFGDADAVQGYVPQ--- |
| SEQ ID NO:28 | NmeningitA | 61 | RAREYLAQQMEQYFFGDADAVQGYVPQ--- |
| SEQ ID NO:29 | Bmallei | 61 | RARQYLMKQTEKYFFGEGADQASGYVP---- |
| SEQ ID NO:30 | Bpseudomallei | 61 | RARQYLMKQTEKYFFGEGADQASGYVP---- |
| SEQ ID NO:31 | Tferrooxidans | 61 | KSRTFLEKQMEAYFFGDGAQSPEGYVP---- |
| SEQ ID NO:32 | Mcapsulatus | 61 | SARKFLEQEREKELFGGGTSTPQGYVP---- |
| SEQ ID NO:33 | Cburneti | 61 | KARQFLEQEMINELFGTGSEKPAGYTSE--- |

Fig. 1A (continued)

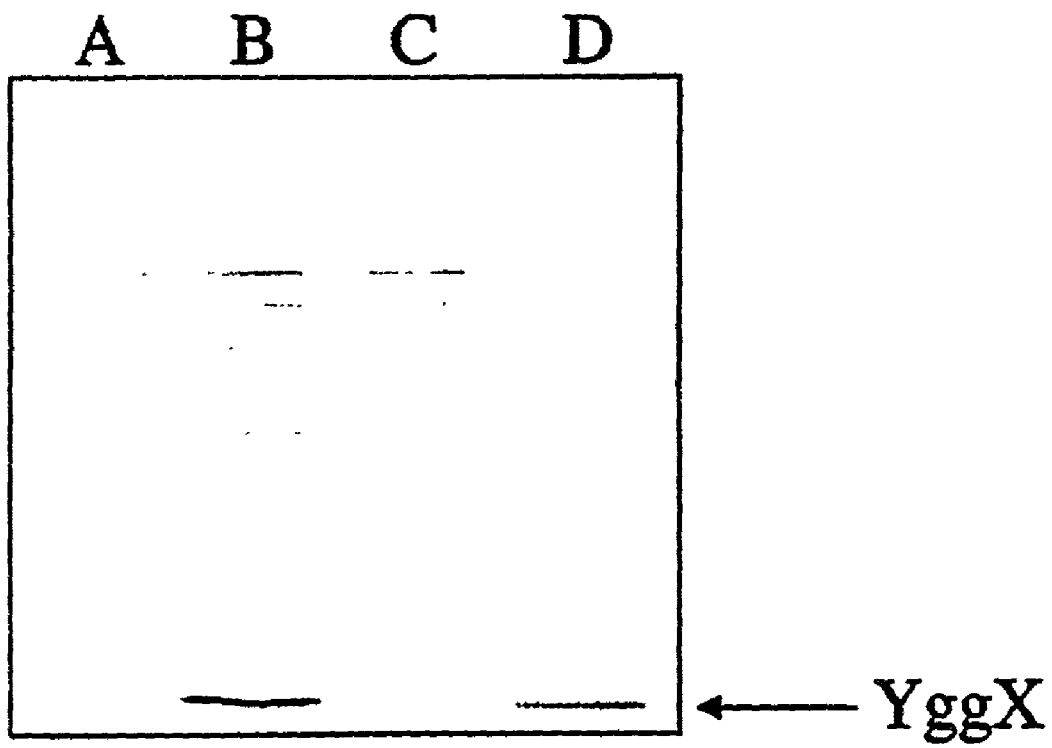

Fig. 2. Increased levels of YggX protein in yggX* mutant. Western blot analysis was performed according to Harlow and Lane (59). Proteins were visualized by using alkaline phosphatase conjugated to anti-rabbit secondary antibody (Promega). Lanes A–C were loaded with crude cell-free extracts (1 μg protein) from strains DM5104, DM5105 (yggX*), and DM5647 (yggX::Gm), respectively. Lane D was loaded with 1 ng purified YggX.

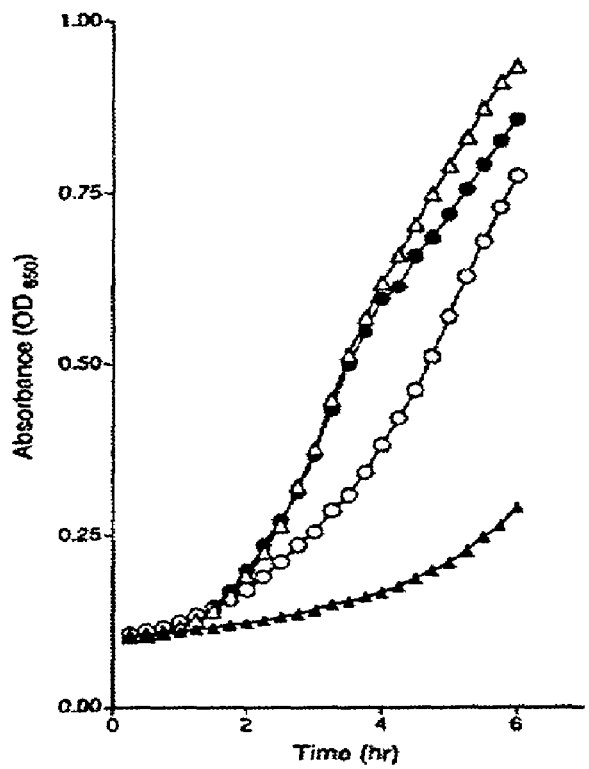
Fig. 3. The yggX* mutation does not increase MNNG resistance of gshA mutants. Strain LT2 was grown in LB with (▲) and without (△) 60 μM MNNG. Both gshA (○) and gshA yggX* (●) mutant strains were grown in LB with 60 μM MNNG.

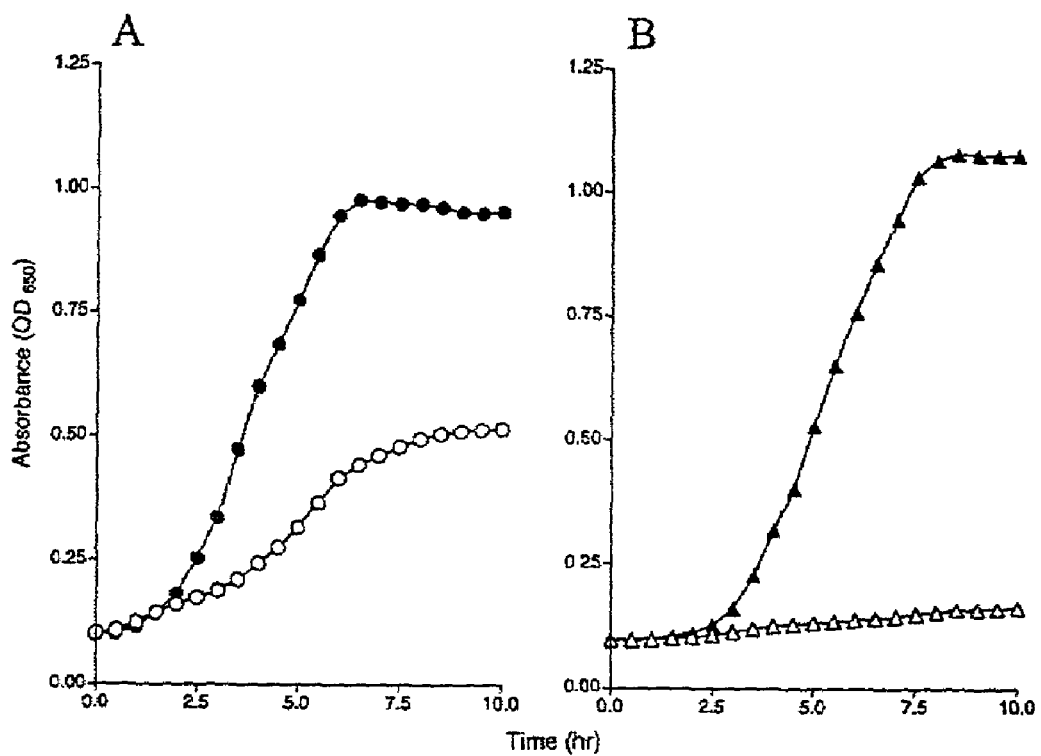
Fig. 4. The yggX* mutation increases resistance of S. enterica to PQ. (A) Growth of gshA (○) and gshA yggX* (●) mutant strains in LB with 4 µM PQ. (B) Growth of LT2 (△) and yggX* (▲) strains in LB with 40 µM PQ.

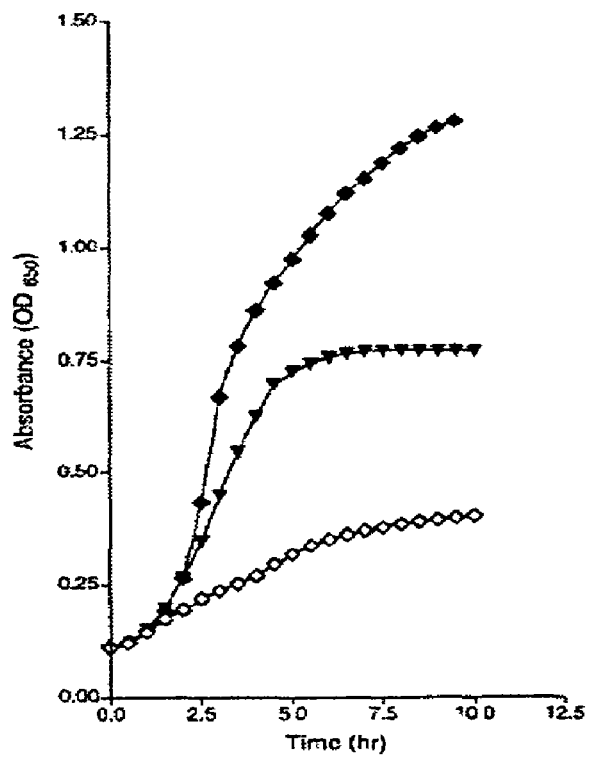
Fig. 5. yggX* does not require soxR to mediate resistance to PQ. Strains LT2 (♦), soxR (◇), and soxR yggX* (▼) were grown in LB with 4.0 μM PQ.

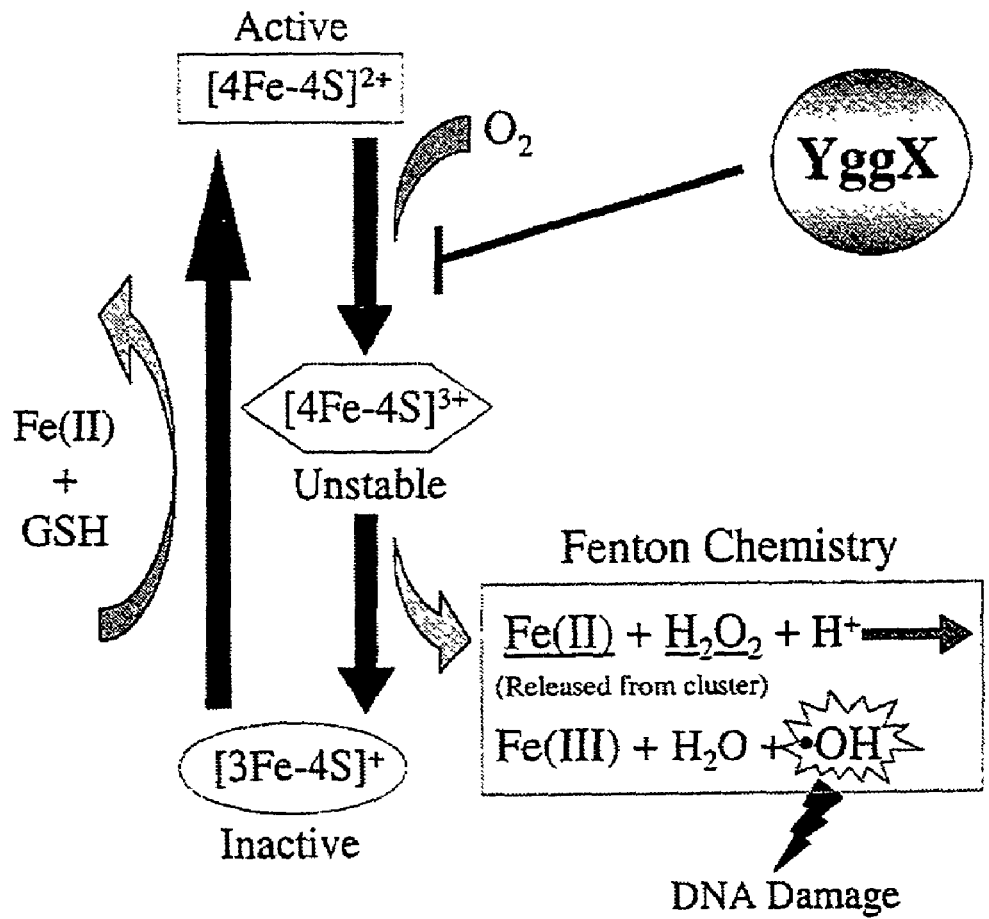
Fig. 6. Model showing how YggX protects *S. enterica* from oxidative damage. The result of superoxide attack on [Fe-S] clusters is depicted. We hypothesize that YggX is able to block oxidative damage to labile clusters and thus prevent the normal downstream consequences of such oxidation.

SEQUENCE LISTING

```
<160> NUMBER OF SEQ ID NOS: 45

<210> SEQ ID NO 1
<211> LENGTH: 65
<212> TYPE: PRT
<213> ORGANISM: Artificial
<220> FEATURE:
<223> OTHER INFORMATION: synthetic YggX consensus sequence
<220> FEATURE:
<221> NAME/KEY: UNSURE
<222> LOCATION: (2)..(2)
<223> OTHER INFORMATION: can be any amino acid
<220> FEATURE:
<221> NAME/KEY: UNSURE
<222> LOCATION: (4)..(6)
<223> OTHER INFORMATION: can be any amino acid
```

```
-continued

<220> FEATURE:
<221> NAME/KEY: UNSURE
<222> LOCATION: (8)..(22)
<223> OTHER INFORMATION: can be any amino acid
<220> FEATURE:
<221> NAME/KEY: UNSURE
<222> LOCATION: (24)..(26)
<223> OTHER INFORMATION: can be any amino acid
<220> FEATURE:
<221> NAME/KEY: UNSURE
<222> LOCATION: (28)..(38)
<223> OTHER INFORMATION: can be any amino acid
<220> FEATURE:
<221> NAME/KEY: UNSURE
<222> LOCATION: (40)..(41)
<223> OTHER INFORMATION: can be any amino acid
<220> FEATURE:
<221> NAME/KEY: UNSURE
<222> LOCATION: (43)..(45)
<223> OTHER INFORMATION: can be any amino acid
<220> FEATURE:
<221> NAME/KEY: UNSURE
<222> LOCATION: (48)..(48)
<223> OTHER INFORMATION: can be any amino acid
<220> FEATURE:
<221> NAME/KEY: UNSURE
<222> LOCATION: (50)..(50)
<223> OTHER INFORMATION: can be any amino acid
<220> FEATURE:
<221> NAME/KEY: UNSURE
<222> LOCATION: (53)..(54)
<223> OTHER INFORMATION: can be any amino acid
<220> FEATURE:
<221> NAME/KEY: UNSURE
<222> LOCATION: (56)..(62)
<223> OTHER INFORMATION: can be any amino acid
<220> FEATURE:
<221> NAME/KEY: UNSURE
<222> LOCATION: (64)..(65)
<223> OTHER INFORMATION: can be any amino acid

<400> SEQUENCE: 1

Met Xaa Arg Xaa Xaa Cys Xaa Xaa Xaa Xaa Xaa Xaa Xaa Xaa
 1               5                  10                  15

Xaa Xaa Xaa Xaa Xaa Xaa Pro Xaa Xaa Xaa Gly Xaa Xaa Xaa Xaa
            20                  25                  30

Xaa Xaa Xaa Xaa Xaa Xaa Trp Xaa Xaa Trp Xaa Xaa Xaa Gln Thr Xaa
         35                  40                  45

Leu Xaa Asn Glu Xaa Xaa Leu Xaa Xaa Xaa Xaa Xaa Xaa Arg Xaa
     50                  55                  60

Xaa
65

<210> SEQ ID NO 2
<211> LENGTH: 87
<212> TYPE: PRT
<213> ORGANISM: Bordetella pertussis

<400> SEQUENCE: 2

Met Ser Arg Ile Val Asn Cys Val Lys Leu Lys Arg Glu Ala Glu Gly
 1               5                  10                  15

Leu Asp Phe Pro Pro Tyr Pro Gly Glu Leu Gly Thr Arg Ile Trp Gln
            20                  25                  30

Gln Ile Ser Lys Glu Ala Trp Glu Trp Lys Gln Ile Gln Thr Arg
         35                  40                  45

Leu Val Asn Glu Asn Arg Leu Asn Leu Ala Asp Ala Arg Ala Arg Lys
     50                  55                  60

Tyr Leu Gln Gln Gln Met Glu Arg Phe Leu Phe Glu Asp Gly Thr Val
```

```
                65                  70                  75                  80
Glu Ala Gln Gly Tyr Val Pro
                85

<210> SEQ ID NO 3
<211> LENGTH: 87
<212> TYPE: PRT
<213> ORGANISM: Bordetella parapertussis

<400> SEQUENCE: 3

Met

His Ile Glu Gly Tyr Thr Pro Pro Glu Ala Lys
            85                  90

<210> SEQ ID NO 6
<211> LENGTH: 87
<212> TYPE: PRT
<213> ORGANISM: Pasteurella multocida

<400> SEQUENCE: 6

Met Ala Arg Thr Val Phe Cys Glu Tyr Leu Lys Gln Glu Ser Glu Gly
1               5                   10                  15

Leu Asp Phe Gln Leu Tyr Pro Gly Glu Leu Gly Lys Arg Ile Phe Asp
            20                  25                  30

Ser Ile Ser Lys Gln Ala Trp Arg Glu Trp Met Lys Lys Gln Thr Met
        35                  40                  45

Leu Val Asn Glu Lys Lys Leu Asn Met Met Asn Ala Asp His Arg Gln
    50                  55                  60

Leu Leu Glu Gln Glu Met Val Asn Phe Leu Phe Glu Gly Lys Asp Val
65                  70                  75                  80

His Ile Glu Gly Tyr Val Pro
            85

<210> SEQ ID NO 7
<211> LENGTH: 87
<212> TYPE: PRT
<213> ORGANISM: Haemophilus influenzae

<400> SEQUENCE: 7

Met Ala Arg Thr Val Phe Cys Glu Tyr Leu Lys Lys Glu Ala Glu Gly
1               5                   10                  15

Leu Asp Phe Gln Leu Tyr Pro Gly Glu Leu Gly Lys Arg Ile Phe Asp
            20                  25                  30

Ser Val Ser Lys Gln Ala Trp Gly Glu Trp Ile Lys Lys Gln Thr Met
        35                  40                  45

Leu Val Asn Glu Lys Lys Leu Asn Met Met Asn Ala Glu His Arg Lys
    50                  55                  60

Leu Leu Glu Gln Glu Met Val Asn Phe Leu Phe Glu Gly Lys Asp Val
65                  70                  75                  80

His Ile Glu Gly Tyr Val Pro
            85

<210> SEQ ID NO 8
<211> LENGTH: 87
<212> TYPE: PRT
<213> ORGANISM: Haemophilus ducreyi

<400> SEQUENCE: 8

Met Ala Arg Met Val Phe Cys Glu Tyr Leu Lys Lys Glu Ala Glu Gly
1               5                   10                  15

Leu Asp Phe Gln Leu Tyr Pro Gly Glu Leu Gly Lys Arg Ile Phe Asn
            20                  25                  30

Ser Ile Ser Lys Gln Ala Trp Ala Glu Trp Ile Lys Lys Gln Thr Met
        35                  40                  45

Leu Val Asn Glu Lys Lys Leu Asn Met Met Asn Pro Glu His Arg Gln
    50                  55                  60

Leu Leu Glu Ala Glu Met Val Asn Phe Leu Phe Glu Gly Lys Asp Val
65                  70                  75                  80

```
His Ile Asp Gly Tyr Val Pro
                85

<210> SEQ ID NO 9
<211> LENGTH: 88
<212> TYPE: PRT
<213> ORGANISM: Shewanella putrefaciens

<400> SEQUENCE: 9

Met Ala Arg Thr Val Asn Cys Val His Leu Asn Lys Glu Ala Asp Gly
1               5                   10                  15

Leu Asp Phe Gln Leu Tyr Pro Gly Asp Leu Gly Lys Arg Ile Phe Asp
                20                  25                  30

Asn Ile Ser Lys Glu Ala Trp Gly Leu Trp Gln Lys Lys Gln Thr Met
            35                  40                  45

Leu Ile Asn Glu Lys Lys Leu Asn Met Met Asn Val Asp Asp Arg Lys
    50                  55                  60

Phe Leu Glu Ala Gln Met Thr Ser Phe Leu Phe Glu Gly Lys Asp Val
65                  70                  75                  80

Glu Ile Glu Gly Phe Val Pro Glu
                85

<210> SEQ ID NO 10
<211> LENGTH: 90
<212> TYPE: PRT
<213> ORGANISM: Vibrio cholerae

<400> SEQUENCE: 10

Met Ala Arg Thr Val Phe Cys Thr Arg Leu Gln Lys Glu Ala Asp Gly
1               5                   10                  15

Leu Asp Phe Gln Leu Tyr Pro Gly Glu Leu Gly Lys Arg Ile Phe Asp
                20                  25                  30

Asn Ile Cys Lys Glu Ala Trp Ala Gln Trp Gln Thr Lys Gln Thr Met
            35                  40                  45

Leu Ile Asn Glu Lys Lys Leu Asn Met Met Asp Pro Glu His Arg Lys
    50                  55                  60

Leu Leu Glu Gln Glu Met Val Asn Phe Leu Phe Glu Gly Lys Glu Val
65                  70                  75                  80

His Ile Glu Gly Tyr Thr Pro Pro Ala Lys
                85                  90

<210> SEQ ID NO 11
<211> LENGTH: 91
<212> TYPE: PRT
<213> ORGANISM: Escherichia coli K-12 MG1655

<400> SEQUENCE: 11

Met Ser Arg Thr Ile Phe Cys Thr Phe Leu Gln Arg Glu Ala Glu Gly
1               5                   10                  15

Gln Asp Phe Gln Leu Tyr Pro Gly Glu Leu Gly Lys Arg Ile Tyr Asn
                20                  25                  30

Glu Ile Ser Lys Glu Ala Trp Ala Gln Trp Gln His Lys Gln Thr Met
            35                  40                  45

Leu Ile Asn Glu Lys Lys Leu Asn Met Met Asn Ala Glu His Arg Lys
    50                  55                  60

Leu Leu Glu Gln Glu Met Val Asn Phe Leu Phe Glu Gly Lys Glu Val
65                  70                  75                  80

His Ile Glu Gly Tyr Thr Pro Glu Asp Lys Lys
```

-continued

<210> SEQ ID NO 12
<211> LENGTH: 91
<212> TYPE: PRT
<213> ORGANISM: Escherichia coli O157:H7EDL933

<400> SEQUENCE: 12

Met Ser Arg Thr Ile Phe Cys Thr Phe Leu Gln Arg Glu Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Glu Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Asn Phe Leu Phe Glu Gly Lys Glu Val
65                  70                  75                  80

His Ile Glu Gly Tyr Thr Pro Glu Asp Lys Lys
                85                  90

<210> SEQ ID NO 13
<211> LENGTH: 91
<212> TYPE: PRT
<213> ORGANISM: Escherichia coli O157:H7

<400> SEQUENCE: 13

Met Ser Arg Thr Ile Phe Cys Thr Phe Leu Gln Arg Glu Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Glu Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Asn Phe Leu Phe Glu Gly Lys Glu Val
65                  70                  75                  80

His Ile Glu Gly Tyr Thr Pro Glu Asp Lys Lys
                85                  90

<210> SEQ ID NO 14
<211> LENGTH: 91
<212> TYPE: PRT
<213> ORGANISM: Salmonella paratyphi

<400> SEQUENCE: 14

Met Ser Arg Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Glu Gly Lys Asp Val
65                  70                  75                  80

His Ile Glu Gly Tyr Thr Pro Glu Asp Lys Lys
                85                  90

<210> SEQ ID NO 15
<211> LENGTH: 88
<212> TYPE: PRT
<213> ORGANISM: Salmonella enteritidis

<400> SEQUENCE: 15

Met Ser Pro Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Glu Gly Lys Asp Val
65                  70                  75                  80

His Ile Glu Gly Tyr Thr Pro Glu
                85

<210> SEQ ID NO 16
<211> LENGTH: 91
<212> TYPE: PRT
<213> ORGANISM: Salmonella dublin

<400> SEQUENCE: 16

Met Ser Pro Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Glu Gly Lys Asp Val
65                  70                  75                  80

His Ile Glu Gly Tyr Thr Pro Glu Asp Lys Lys
                85                  90

<210> SEQ ID NO 17
<211> LENGTH: 91
<212> TYPE: PRT
<213> ORGANISM: Salmonella typhi CT18

<400> SEQUENCE: 17

Met Ser Arg Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Glu Gly Lys Asp Val
65                  70                  75                  80

His Ile Glu Gly Tyr Thr Pro Glu Asp Lys Lys
                85                  90

<210> SEQ ID NO 18
<211> LENGTH: 91
<212> TYPE: PRT
<213> ORGANISM: Salmonella typhimurium

<400> SEQUENCE: 18

Met Ser Arg Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Gly Lys Asp Val
65                  70                  75                  80

His Ile Glu Gly Tyr Pro Thr Glu Asp Lys Lys
            85                  90

<210> SEQ ID NO 19
<211> LENGTH: 78
<212> TYPE: PRT
<213> ORGANISM: Klebsiella pneumoniae

<400> SEQUENCE: 19

Met Ser Arg Thr Ile Phe Cys Thr Phe Leu Gln Arg Glu Ala Asp Gly
1               5                   10                  15

Gln Asp Phe Gln Leu Tyr Pro Gly Glu Leu Gly Lys Arg Ile Tyr Asn
            20                  25                  30

Glu Ile Ser Lys Glu Ala Trp Ala Gln Trp Gln His Lys Gln Thr Met
        35                  40                  45

Leu Ile Asn Glu Lys Lys Leu Ser Met Met Asn Pro Glu His Arg Lys
    50                  55                  60

Leu Leu Glu Gln Glu Met Val Gln Phe Leu Phe Glu Gly Lys
65                  70                  75

<210> SEQ ID NO 20
<211> LENGTH: 90
<212> TYPE: PRT
<213> ORGANISM: Yersinia pestis

<400> SEQUENCE: 20

Met Ser Arg Thr Ile Phe Cys Thr Phe Leu Lys Lys Asp Ala Glu Arg
1               5                   10                  15

Gln Asp Phe Gln Leu Tyr Pro Gly Glu Ile Gly Lys Arg Ile Tyr Asn
            20                  25                  30

Glu Ile Ser Lys Glu Ala Trp Ser Gln Trp Ile Thr Lys Gln Thr Met
        35                  40                  45

Leu Ile Asn Glu Lys Lys Leu Ser Met Met Asn Ile Glu Asp Arg Lys
    50                  55                  60

Leu Leu Glu Gln Glu Met Val Asn Phe Leu Phe Glu Gly Gln Asp Val
65                  70                  75                  80

His Ile Ala Gly Tyr Thr Pro Pro Ser Lys
            85                  90

<210> SEQ ID NO 21
<211> LENGTH: 76
<212> TYPE: PRT

<213> ORGANISM: Buchnera sp. APS

<400> SEQUENCE: 21

Met Asn Arg Ile Ile Phe Cys Thr Phe Phe Lys Lys Ser Glu Gly
1               5                   10                  15

Gln Asp Phe Gln Ser Tyr Pro Gly Lys Leu Gly Lys Lys Ile Tyr Asp
                20                  25                  30

Gln Ile Ser Lys Lys Ala Trp Glu Lys Trp Ile Glu Lys Gln Thr Ile
            35                  40                  45

Leu Ile Asn Glu Glu Asn Leu Asn Met Phe Asn Leu Glu His Arg Lys
        50                  55                  60

Lys Ile Glu Lys Tyr Met Lys Leu Phe Leu Phe Lys
65                  70                  75

<210> SEQ ID NO 22
<211> LENGTH: 89
<212> TYPE: PRT
<213> ORGANISM: Xylella fastidiosa

<400> SEQUENCE: 22

Met Gln Arg Ile Ile Phe Cys Glu Tyr Glu Gln Arg Asp Thr Glu Gly
1               5                   10                  15

Leu Asp Phe Val Pro Tyr Pro Gly Gly Leu Gly Gln Lys Ile Phe Ala
                20                  25                  30

Cys Ile Gly Lys Val Gly Trp Ala Ala Trp Leu Val His Gln Thr Met
            35                  40                  45

Leu Ile Asn Glu Asn Arg Leu Ser Pro Arg Asn Pro Ser His Arg Ala
        50                  55                  60

Phe Leu Glu Glu Glu Leu Asn Lys Phe Leu Phe Glu Arg Arg Val Ala
65                  70                  75                  80

Lys Pro Glu Gly Tyr Ile Glu Pro Asp
                85

<210> SEQ ID NO 23
<211> LENGTH: 90
<212> TYPE: PRT
<213> ORGANISM: Pseudomonas syringae

<400> SEQUENCE: 23

Met Thr Arg Thr Val Met Cys Arg Lys Tyr Lys Glu Glu Leu Pro Gly
1               5                   10                  15

Leu Glu Arg Ala Pro Tyr Pro Gly Ala Lys Gly Glu Asp Ile Phe Asn
                20                  25                  30

His Val Ser Gln Lys Ala Trp Ala Asp Trp Gln Lys His Gln Thr Leu
            35                  40                  45

Leu Ile Asn Glu Arg Arg Leu Asn Met Met Asn Ala Glu Asp Arg Lys
        50                  55                  60

Phe Leu Gln Thr Glu Met Asp Lys Phe Leu Ser Gly Glu Glu Tyr Ala
65                  70                  75                  80

Gln Ala Glu Gly Tyr Val Pro Pro Glu Lys
                85                  90

<210> SEQ ID NO 24
<211> LENGTH: 87
<212> TYPE: PRT
<213> ORGANISM: Pseudomonas putida

<400> SEQUENCE: 24

```
Met Thr Arg Thr Val Met Cys Arg Lys Tyr Gln Glu Leu Pro Gly
1               5                   10                  15

Leu Glu Arg Pro Pro Tyr Pro Gly Ala Lys Gly Gln Asp Ile Phe Glu
                20                  25                  30

His Ile Ser Gln Lys Ala Trp Ala Asp Trp Gln Lys His Gln Thr Met
            35                  40                  45

Leu Ile Asn Glu Lys Arg Leu Asn Met Met Asn Ala Glu Asp Arg Lys
        50                  55                  60

Phe Leu Gln Ala Glu Met Asp Lys Phe Phe Ala Gly Glu Tyr Ala
65                  70                  75                  80

Gln Ala Glu Gly Tyr Val Pro
                85
```

```
<210> SEQ ID NO 25
<211> LENGTH: 87
<212> TYPE: PRT
<213> ORGANISM: Pseudomonas aeruginosa

<400> SEQUENCE: 25

Met Ser Arg Thr Val Met Cys Arg Lys Tyr His Glu Leu Pro Gly
1               5                   10                  15

Leu Asp Arg Pro Pro Tyr Pro Gly Ala Lys Gly Glu Asp Ile Tyr Asn
                20                  25                  30

Asn Val Ser Arg Lys Ala Trp Asp Glu Trp Gln Lys His Gln Thr Met
            35                  40                  45

Leu Ile Asn Glu Arg Arg Leu Asn Met Met Asn Ala Glu Asp Arg Lys
        50                  55                  60

Phe Leu Gln Gln Glu Met Asp Lys Phe Leu Ser Gly Glu Asp Tyr Ala
65                  70                  75                  80

Lys Ala Asp Gly Tyr Val Pro
                85
```

```
<210> SEQ ID NO 26
<211> LENGTH: 88
<212> TYPE: PRT
<213> ORGANISM: Neisseria gonorrhoeae

<400> SEQUENCE: 26

Met Ala Arg Met Val Phe Cys Val Lys Leu Asn Lys Glu Ala Glu Gly
1               5                   10                  15

Met Lys Phe Pro Pro Leu Pro Asn Glu Leu Gly Lys Arg Ile Phe Glu
                20                  25                  30

Asn Val Ser Gln Glu Ala Trp Ala Ala Trp Thr Arg His Gln Thr Met
            35                  40                  45

Leu Ile Asn Glu Asn Arg Leu Ser Leu Ala Asp Pro Arg Ala Arg Glu
        50                  55                  60

Tyr Leu Ala Gln Gln Met Glu Gln Tyr Phe Phe Gly Asp Gly Ala Asp
65                  70                  75                  80

Ala Val Gln Gly Tyr Val Pro Gln
                85
```

```
<210> SEQ ID NO 27
<211> LENGTH: 88
<212> TYPE: PRT
<213> ORGANISM: Neisseria meningitidis B

<400> SEQUENCE: 27

Met Ala Arg Met Val Phe Cys Val Lys Leu Asn Lys Glu Ala Glu Gly
```

```
                 1               5                  10                 15
Met Lys Phe Pro Pro Leu Pro Asn Glu Leu Gly Lys Arg Ile Phe Glu
                20                 25                 30

Asn Val Ser Gln Glu Ala Trp Ala Ala Trp Thr Arg His Gln Thr Met
                35                 40                 45

Leu Ile Asn Glu Asn Arg Leu Ser Leu Ala Asp Pro Arg Ala Arg Glu
    50                  55                 60

Tyr Leu Ala Gln Gln Met Glu Gln Tyr Phe Phe Gly Asp Gly Ala Asp
65                  70                 75                  80

Ala Val Gln Gly Tyr Val Pro Gln
                85

<210> SEQ ID NO 28
<211> LENGTH: 88
<212> TYPE: PRT
<213> ORGANISM: Neisseria meningitidis A

<400> SEQUENCE: 28

Met Ala Arg Met Val Phe Cys Val Lys Leu Asn Lys Glu Ala Glu Gly
1               5                  10                 15

Met Lys Phe Pro Pro Leu Pro Asn Glu Leu Gly Lys Arg Ile Phe Glu
                20                 25                 30

Asn Val Ser Gln Glu Ala Trp Ala Ala Trp Thr Arg His Gln Thr Met
                35                 40                 45

Leu Ile Asn Glu Asn Arg Leu Ser Leu Ala Asp Pro Arg Ala Arg Glu
    50                  55                 60

Tyr Leu Ala Gln Gln Met Glu Gln Tyr Phe Phe Gly Asp Gly Ala Asp
65                  70                 75                  80

Ala Val Gln Gly Tyr Val Pro Gln
                85

<210> SEQ ID NO 29
<211> LENGTH: 87
<212> TYPE: PRT
<213> ORGANISM: Burkholderia mallei

<400> SEQUENCE: 29

Met Ala Arg Met Ile His Cys Ala Lys Leu Gly Lys Glu Ala Glu Gly
1               5                  10                 15

Leu Asp Phe Pro Pro Leu Pro Gly Glu Leu Gly Lys Arg Leu Tyr Glu
                20                 25                 30

Ser Val Ser Lys Gln Ala Trp Gln Asp Trp Leu Lys Gln Gln Thr Met
                35                 40                 45

Leu Ile Asn Glu Asn Arg Leu Asn Met Ala Asp Pro Arg Ala Arg Gln
    50                  55                 60

Tyr Leu Met Lys Gln Thr Glu Lys Tyr Phe Phe Gly Glu Gly Ala Asp
65                  70                 75                  80

Gln Ala Ser Gly Tyr Val Pro
                85

<210> SEQ ID NO 30
<211> LENGTH: 87
<212> TYPE: PRT
<213> ORGANISM: Burkholderia pseudomallei

<400> SEQUENCE: 30

Met Ala Arg Met Ile His Cys Ala Lys Leu Gly Lys Glu Ala Glu Gly
1               5                  10                 15
```

Leu Asp Phe Pro Pro Leu Pro Gly Glu Leu Gly Lys Arg Leu Tyr Glu
            20                  25                  30

Ser Val Ser Lys Gln Ala Trp Gln Asp Trp Leu Lys Gln Gln Thr Met
            35                  40                  45

Leu Ile Asn Glu Asn Arg Leu Asn Met Ala Asp Pro Arg Ala Arg Gln
            50                  55                  60

Tyr Leu Met Lys Gln Thr Glu Lys Tyr Phe Phe Gly Glu Gly Ala Asp
65                  70                  75                  80

Gln Ala Ser Gly Tyr Val Pro
                85

<210> SEQ ID NO 31
<211> LENGTH: 87
<212> TYPE: PRT
<213> ORGANISM: Thiobacillus ferrooxidans

<400> SEQUENCE: 31

Met Ser Arg Met Val Gln Cys Val Lys Leu Gly His Glu Ala Glu Gly
1               5                   10                  15

Leu Asp Arg Pro Pro Tyr Pro Gly Ala Leu Gly Ala Arg Ile Tyr Gln
            20                  25                  30

Glu Val Ser Lys Glu Ala Trp Gln Gly Trp Leu Lys His Gln Thr Met
            35                  40                  45

Leu Ile Asn Glu Tyr Arg Leu Ser Pro Ile Asp Pro Lys Ser Arg Thr
            50                  55                  60

Phe Leu Glu Lys Gln Met Glu Ala Tyr Phe Phe Gly Asp Gly Ala Gln
65                  70                  75                  80

Ser Pro Glu Gly Tyr Val Pro
                85

<210> SEQ ID NO 32
<211> LENGTH: 87
<212> TYPE: PRT
<213> ORGANISM: Methylococcus capsulatus

<400> SEQUENCE: 32

Met Ala Arg Arg Ile Ile Cys Ala Lys Leu Gly Ile Glu Ala Asp Gly
1               5                   10                  15

Leu Asp Ala Pro Pro Phe Pro Gly Pro Gln Gly Gln Arg Ile Phe Glu
            20                  25                  30

His Val Ser Lys Glu Ala Trp Gln Asp Trp Leu Lys Leu Gln Thr Met
            35                  40                  45

Leu Ile Asn Glu His Arg Leu Thr Pro Phe Glu Ala Ser Ala Arg Lys
            50                  55                  60

Phe Leu Glu Gln Glu Arg Glu Lys Phe Leu Phe Gly Gly Thr Ser
65                  70                  75                  80

Thr Pro Gln Gly Tyr Val Pro
                85

<210> SEQ ID NO 33
<211> LENGTH: 88
<212> TYPE: PRT
<213> ORGANISM: Coxiella burnetii

<400> SEQUENCE: 33

Met Thr Arg Arg Ile Ile Cys Gln Lys Leu Gly Lys Glu Ala Asp Ala
1               5                   10                  15

-continued

Leu Asn Tyr Ser Pro Tyr Pro Gly Glu Leu Gly Glu Arg Ile Tyr Asn
            20                  25                  30

His Ile Ser Glu Gln Ala Trp Gln Ala Trp Leu Ser His Gln Thr Met
        35                  40                  45

Leu Ile Asn Glu Tyr Arg Leu Ser Leu Ile Asp Pro Lys Ala Arg Gln
    50                  55                  60

Phe Leu Glu Gln Glu Met Ile Asn Phe Leu Phe Gly Thr Gly Ser Glu
65                  70                  75                  80

Lys Pro Ala Gly Tyr Thr Ser Glu
                85

<210> SEQ ID NO 34
<211> LENGTH: 91
<212> TYPE: PRT
<213> ORGANISM: Salmonella typhimurium

<400> SEQUENCE: 34

Met Ser Arg Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Glu Gly Lys Asp Val
65                  70                  75                  80

His Ile Glu Gly Tyr Thr Pro Glu Asp Lys Lys
                85                  90

<210> SEQ ID NO 35
<211> LENGTH: 91
<212> TYPE: PRT
<213> ORGANISM: Salmonella typhi

<400> SEQUENCE: 35

Met Ser Arg Thr Ile Phe Cys Thr Tyr Leu Gln Arg Asp Ala Glu Gly
1               5                   10                  15

Gln Asp Phe Gln Leu Tyr Pro Gly Glu Leu Gly Lys Arg Ile Tyr Asn
            20                  25                  30

Glu Ile Ser Lys Asp Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Ser Phe Leu Phe Glu Gly Lys Asp Val
65                  70                  75                  80

His Ile Glu Gly Tyr Thr Pro Glu Asp Lys Lys
                85                  90

<210> SEQ ID NO 36
<211> LENGTH: 91
<212> TYPE: PRT
<213> ORGANISM: Escherichia coli

<400> SEQUENCE: 36

Met Ser Arg Thr Ile Phe Cys Thr Phe Leu Gln Arg Glu Ala Glu Gly
1               5                   10                  15

Gln Asp Phe Gln Leu Tyr Pro Gly Glu Leu Gly Lys Arg Ile Tyr Asn

-continued

```
            20                  25                  30
Glu Ile Ser Lys Glu Ala Trp Ala Gln Trp Gln His Lys Gln Thr Met
        35                  40                  45

Leu Ile Asn Glu Lys Lys Leu Asn Met Met Asn Ala Glu His Arg Lys
    50                  55                  60

Leu Leu Glu Gln Glu Met Val Asn Phe Leu Phe Glu Gly Lys Glu Val
65                  70                  75                  80

His Ile Glu Gly Tyr Thr Pro Glu Asp Lys Lys
                85                  90

<210> SEQ ID NO 37
<211> LENGTH: 90
<212> TYPE: PRT
<213> ORGANISM: Yersinia pestis

<400> SEQUENCE: 37

Met Ser Arg Thr Ile Phe Cys Thr Phe Leu Lys Lys Asp Ala Glu Arg
1               5                   10                  15

Gln Asp Phe Gln Leu Tyr Pro Gly Glu Ile Gly Lys Arg Ile Tyr Asn
            20                  25                  30

Glu Ile Ser Lys Glu Ala Trp Ser Gln Trp Ile Thr Lys Gln Thr Met
        35                  40                  45

Leu Ile Asn Glu Lys Lys Leu Ser Met Met Asn Ile Glu Asp Arg Lys
    50                  55                  60

Leu Leu Glu Gln Glu Met Val Asn Phe Leu Phe Glu Gly Gln Asp Val
65                  70                  75                  80

His Ile Ala Gly Tyr Thr Pro Pro Ser Lys
                85                  90

<210> SEQ ID NO 38
<211> LENGTH: 87
<212> TYPE: PRT
<213> ORGANISM: Haemophilus influenzae

<400> SEQUENCE: 38

Met Ala Arg Thr Val Phe Cys Glu Tyr Leu Lys Lys Glu Ala Glu Gly
1               5                   10                  15

Leu Asp Phe Gln Leu Tyr Pro Gly Glu Leu Gly Lys Arg Ile Phe Asp
            20                  25                  30

Ser Val Ser Lys Gln Ala Trp Gly Glu Trp Ile Lys Lys Gln Thr Met
        35                  40                  45

Leu Val Asn Glu Lys Lys Leu Asn Met Met Asn Ala Glu His Arg Lys
    50                  55                  60

Leu Leu Glu Gln Glu Met Val Asn Phe Leu Phe Glu Gly Lys Asp Val
65                  70                  75                  80

His Ile Glu Gly Tyr Val Pro
                85

<210> SEQ ID NO 39
<211> LENGTH: 88
<212> TYPE: PRT
<213> ORGANISM: Shewanella putrefaciens

<400> SEQUENCE: 39

Met Ala Arg Thr Val Asn Cys Val His Leu Asn Lys Glu Ala Asp Gly
1               5                   10                  15

Leu Asp Phe Gln Leu Tyr Pro Gly Asp Leu Gly Lys Arg Ile Phe Asp
            20                  25                  30

```
Asn Ile Ser Lys Glu Ala Trp Gly Leu Trp Gln Lys Gln Thr Met
         35                  40                  45

Leu Ile Asn Glu Lys Lys Leu Asn Met Met Asn Val Asp Asp Arg Lys
 50                  55                  60

Phe Leu Glu Ala Gln Met Thr Ser Phe Leu Phe Gly Lys Asp Val
 65                  70                  75                  80

Glu Ile Glu Gly Phe Val Pro Glu
                 85

<210> SEQ ID NO 40
<211> LENGTH: 87
<212> TYPE: PRT
<213> ORGANISM: Pseudomonas aeruginosa

<400> SEQUENCE: 40

Met Ser Arg Thr Val Met Cys Arg Lys Tyr His Glu Glu Leu Pro Gly
 1               5                  10                  15

Leu Asp Arg Pro Pro Tyr Pro Gly Ala Lys Gly Glu Asp Ile Tyr Asn
                 20                  25                  30

Asn Val Ser Arg Lys Ala Trp Asp Glu Trp Gln Lys His Gln Thr Met
         35                  40                  45

Leu Ile Asn Glu Arg Arg Leu Asn Met Met Asn Ala Glu Asp Arg Lys
 50                  55                  60

Phe Leu Gln Gln Glu Met Asp Lys Phe Leu Ser Gly Glu Asp Tyr Ala
 65                  70                  75                  80

Lys Ala Asp Gly Tyr Val Pro
                 85

<210> SEQ ID NO 41
<211> LENGTH: 87
<212> TYPE: PRT
<213> ORGANISM: Pseudomonas putida

<400> SEQUENCE: 41

Met Thr Arg Thr Val Met Cys Arg Lys Tyr Gln Glu Glu Leu Pro Gly
 1               5                  10                  15

Leu Glu Arg Pro Pro Tyr Pro Gly Ala Lys Gly Gln Asp Ile Phe Glu
                 20                  25                  30

His Ile Ser Gln Lys Ala Trp Ala Asp Trp Gln Lys His Gln Thr Met
         35                  40                  45

Leu Ile Asn Glu Lys Arg Leu Asn Met Met Asn Ala Glu Asp Arg Lys
 50                  55                  60

Phe Leu Gln Ala Glu Met Asp Lys Phe Phe Ala Gly Glu Glu Tyr Ala
 65                  70                  75                  80

Gln Ala Glu Gly Tyr Val Pro
                 85

<210> SEQ ID NO 42
<211> LENGTH: 88
<212> TYPE: PRT
<213> ORGANISM: Neisseria gonorrhoeae

<400> SEQUENCE: 42

Met Ala Arg Met Val Phe Cys Val Lys Leu Asn Lys Glu Ala Glu Gly
 1               5                  10                  15

Met Lys Phe Pro Pro Leu Pro Asn Glu Leu Gly Lys Arg Ile Phe Glu
                 20                  25                  30
```

-continued

Asn Val Ser Gln Glu Ala Trp Ala Ala Trp Thr Arg His Gln Thr Met
             35                  40                  45

Leu Ile Asn Glu Asn Arg Leu Ser Leu Ala Asp Pro Arg Ala Arg Glu
         50                  55                  60

Tyr Leu Ala Gln Gln Met Glu Gln Tyr Phe Phe Gly Asp Gly Ala Asp
65                  70                  75                  80

Ala Val Gln Gly Tyr Val Pro Gln
                85

<210> SEQ ID NO 43
<211> LENGTH: 87
<212> TYPE: PRT
<213> ORGANISM: Thiobacillus ferrooxidans

<400> SEQUENCE: 43

Met Ser Arg Met Val Gln Cys Val Lys Leu Gly His Glu Ala Glu Gly
1               5                   10                  15

Leu Asp Arg Pro Pro Tyr Pro Gly Ala Leu Gly Ala Arg Ile Tyr Gln
             20                  25                  30

Glu Val Ser Lys Glu Ala Trp Gln Gly Trp Leu Lys His Gln Thr Met
             35                  40                  45

Leu Ile Asn Glu Tyr Arg Leu Ser Pro Ile Asp Pro Lys Ser Arg Thr
         50                  55                  60

Phe Leu Glu Lys Gln Met Glu Ala Tyr Phe Phe Gly Asp Gly Ala Gln
65                  70                  75                  80

Ser Pro Glu Gly Tyr Val Pro
                85

<210> SEQ ID NO 44
<211> LENGTH: 84
<212> TYPE: PRT
<213> ORGANISM: Bordetella bronchiseptica

<400> SEQUENCE: 44

Met Ser Arg Ile Val Asn Cys Val Lys Leu Lys Arg Glu Ala Glu Gly
1               5                   10                  15

Leu Asp Phe Pro Pro Tyr Pro Gly Glu Leu Gly Thr Arg Ile Trp Gln
             20                  25                  30

Gln Ile Ser Lys Glu Ala Trp Glu Trp Lys Gln Ile Gln Thr Arg
             35                  40                  45

Leu Val Asn Glu Asn Arg Leu Asn Pro Ala Asp Ala Arg Ala Arg Lys
         50                  55                  60

Tyr Leu Gln Gln Gln Met Glu Arg Phe Leu Phe Glu Asp Gly Thr Val
65                  70                  75                  80

Glu Ala Gln Gly

<210> SEQ ID NO 45
<211> LENGTH: 89
<212> TYPE: PRT
<213> ORGANISM: Xylella fastidiosa

<400> SEQUENCE: 45

Met Gln Arg Ile Ile Phe Cys Glu Tyr Glu Gln Arg Asp Thr Glu Gly
1               5                   10                  15

Leu Asp Phe Val Pro Tyr Pro Gly Glu Leu Gly Gln Lys Ile Phe Ala
             20                  25                  30

Cys Ile Gly Lys Val Gly Trp Ala Ala Trp Leu Val His Gln Thr Met
             35                  40                  45

```
Leu Ile Asn Glu Asn Arg Leu Ser Pro Arg Asn Pro Ser His Arg Ala
    50                  55                  60

Phe Leu Glu Glu Glu Leu Asn Lys Phe Leu Phe Glu Arg Arg Val Ala
65                  70                  75                  80

Lys Pro Glu Gly Tyr Ile Glu Pro Asp
                85
```

METHOD FOR PREVENTING SUPEROXIDE DAMAGE TO CELLS AND OXYGEN-LABILE PROTEINS

CROSS-REFERENCE TO RELATED APPLICATION

This application claims priority to provisional patent application Ser. No. 60/234,588, filed Sep. 22, 2000, incorporated by reference herein.

STATEMENT REGARDING FEDERALLY SPONSORED RESEARCH OR DEVELOPMENT

This invention was made with United States government support awarded by the following agency: NIH 9723830. The government has certain rights in this invention.

BACKGROUND OF THE INVENTION

Cell physiology is characterized by the interplay of numerous metabolic pathways and processes. Integration is essential to create a metabolism that is robust, yet adaptable to complex environmental conditions, such as growth in the presence or absence of oxygen. Although aerobic respiration provides a substantial energetic advantage, it necessarily generates toxic oxygen species that can damage macromolecules (Gonzalez-Flecha, B. and Demple, B., *J. Biol. Chem.* 270:13681-7, 1995; Imlay, J. A. and Fridovich, I., *J. Biol. Chem.* 266:6957-65,1991. For example, superoxide radicals ($O_2^-$) can oxidize labile [4Fe-4S] to inactive [3Fe-4S] clusters (Flint, D. H., et al., *J. Biol. Chem.* 268:22369-76, 1993; Kuo, C. F., et al., *J. Biol. Chem.* 262:4724-7,1987). Such oxidation has at least two detrimental consequences, inactivation of enzymes containing [Fe—S] clusters (Flint, D. H., et al., supra, 1993; Gardner, P. R. and Fridovich, I., *Arch. Biochem. Biophys.* 284:106-11, 1991; Gardner, P. R. and Fridovich, I., *J Biol Chem* 266:1478-83,1991; Gardner, P. R. and Fridovich, I., *J. Biol. Chem.* 266:19328-33,1991), and increased DNA damage (Imlay, J. A. and Linn, S., *Science* 240:1302-9, 1988; Keyer, K. and Imlay, J. A., *Proc. Natl. Acad. Sci.* USA 93:13635-40,1996). DNA damage results from ferrous ions, released during the oxidation of [4Fe-4S] clusters. These ions participate in Fenton chemistry ($Fe(II) + H_2O_2 + H^+ \rightarrow Fe(III) + H_2O + OH\bullet$), with the hydroxyl radicals damaging DNA and other macromolecules (Keyer, K. and Imlay, J. A., supra, 1996; Liochev, S. I. and Fridovich, I., *Free Radic. Biol. Med.* 16:29-33, 1994; Srinivasan, C., et al., *J. Biol. Chem.* 275:29187-92, 2000). It would not be surprising that many cellular anomalies caused by increased superoxide concentration result from oxidization of [Fe—S] clusters (Keyer, K. and Imlay, J. A., supra, 1996).

Several systems exist to reduce the potential for damage by superoxide radicals (Storz, G. and Imlay, J. A., *Curr. Opin. Microbiol.* 2:188-94, 1999). In general, these systems either prevent the damage from occurring or repair it. The Sox regulon is a good example of the former. This regulon includes a number of genes that are induced under conditions of oxidative stress via the SoxRS regulatory system (Hidalgo, E. and Demple, B., *Embo J.* 16:1056-65,1997; Gaudu, P., et. al., *J. Biol. Chem.* 272:5082-6,1997; Liochev, S. I., et al., J. Biol. Chem. 274:9479-81, 1999). One component of this system is the superoxide dismutase enzymes (SOD, EC 1.15.1.1) that catalyze the formation of molecular oxygen and hydrogen peroxide from two superoxide radicals ($O_2^- + O_2^- + 2H^+ \rightarrow O_2 + H_2O_2$). The resulting hydrogen peroxide ($H_2O_2$) is a substrate for catalase (hydroperoxidase) enzymes (EC 1.11.1.6,1.11.1.7) that convert it to water and molecular oxygen. A distinct way of protecting [Fe—S] clusters is shown by the FeSII protein of *Azotobacter vinelandii*. The FeSII, or Shetna protein, forms a complex with nitrogenase under periods of high oxygen exposure, thus protecting the essential [Fe—S] cluster from oxidation (Lou, J., et al., *Biochemistry* 38:5563-71, 1999; Shethna, Y. I., et al., *Biochem. Biophys. Res. Commun.* 31:862-8,1968).

In addition to eliminating superoxide per se, mechanisms to repair damage incurred by the superoxide radicals have evolved. This second strategy includes multiple repair systems that are specific for DNA damage (McCullough, A. K., et al., *Annu. Rev. Biochem.* 68:255-85,1999; Cadet, J., et al., *Mutat. Res.* 462:121-8, 2000; Boiteux, S. and Radicella, J. P., *Biochimie* 81:59-67,1999). The DNA glycosylase MutY, which itself contains an [Fe—S] cluster (Michaels, M. L., et al., *Nucleic Acids Res.* 18:3841-5, 1990; Porello, S. L., et al., *Biochemistry* 37:6465-75, 1998), recognizes the mispairing of an oxidized guanine base (8-oxo-guanine) with adenine and cleaves the relevant adenine (Michaels, M. L., et al., *Biochemistry* 31:10964-8, 1992). This cleavage product becomes the target for additional repair enzymes that prevent the generation of a G●C to T●A transversion mutation.

Another example involves direct repair of oxidized [Fe—S] clusters in vivo. The enzyme paradigm for the majority of studies addressing the in vivo and in vitro reconstitution of [Fe—S] clusters is aconitase (Acn, EC 4.2.1.3) (Kennedy, M. C. and Beinert, H., *J. Biol. Chem.* 263:8194-8, 1988; Gardner, P. R. and Fridovich, I., *J. Biol. Chem.* 267:8757-63,1992; Gardner, P. R. and Fridovich, I., *Arch. Biochem. Biophys.* 301:98-102, 1993). Part of the catalytic [4Fe-4S] center in aconitase is exposed to the solution and is not sequestered by the enzyme; thus the enzyme is sensitive to attack by superoxide (Gardner, P. R and Fridovich, I., supra, 1992; Beinert, H., et al., *Chem. Rev.* 96:2335-2373, 1996). Although extensive work has been preformed to characterize in vitro reactivation of oxidized [Fe—S] clusters (Kennedy, M. C. and Beinert, H., supra, 1988), the participants in [Fe—S] cluster repair in vivo are less well defined (Gardner, P. R. and Fridovich, I., supra, 1993). The benefit of in vivo repair of [Fe—S] clusters is at least two fold, first the restoration of enzyme activity, and second, the decrease of free iron.

Several experiments have suggested that glutathione (GSH) is involved in the in vivo repair and possibly biosynthesis, of the [Fe—S] center in aconitase (Gardner, P. R. and Fridovich, I., supra, 1993). When *Escherichia coli* strains in vivo were challenged with oxygen total aconitase activity decreased, as expected for an enzyme with a labile [Fe—S] cluster. However, when the oxygen challenge was removed, unlike the wild-type strain, gshA (encodes y-I-glutamyl-I-cysteine synthetase, EC 6.3.2.2) mutants were unable to regain aconitase activity in the absence of protein synthesis (Gardner, P. R. and Fridovich, I., supra, 1993).

Further, gshA mutants of *E. coli* have reduced total aconitase activity (Gardner, P. R. and Fridovich, I., supra, 1993).

Needed in the art is an improved method of protecting cells and oxygen-labile enzymes from superoxide damage.

BRIEF SUMMARY OF THE INVENTION

We disclose herein that increased levels of the YggX protein reverse several metabolic defects attributed to a lack of GSH, increase resistance to superoxide stress, and decrease the spontaneous mutation frequency in *S. enterica*.

The phenotypic consequences of increased YggX protein are consistent with a model in which this protein protects labile [Fe—S] clusters from oxidative damage.

In one embodiment, the present invention is a method of reducing superoxide damage to a cell, comprising the step of engineering the cell to produce more than the native amount of the YggX protein or its homolog, wherein the cells are rendered more resistant to oxidative damage. A preferred method additionally comprises the step of analyzing the protein to determine that the cells are rendered more resistant to superoxide damage.

Another embodiment of the present invention comprises increasing the resistance of oxygen-labile proteins to oxidative damage, comprising the step of co-expressing the oxygen-labile protein with the YggX protein or a homolog of the YggX protein. Preferably, one additionally examines the oxygen-labile protein to determine the amount of superoxide damage.

Another embodiment of the present invention comprises a method of screening compounds for antibiotic properties, comprising the step of examining a test compound's ability to effect YggX activity or the activity of a YggX homolog, wherein decreased YggX activity indicates that the compound is a likely candidate as an antibiotic.

It is an object of the present invention to protect cell and oxygen-labile proteins from superoxide damage.

Other objects, features and advantages of the present invention will become apparent to one of skill in the art after review of the specification, claims and drawings.

BRIEF DESCRIPTION OF THE SEVERAL VIEWS OF THE DRAWINGS

FIG. 1. Physical parameters of yggX and its gene product. (A) Alignment of YggX homologs. (B) Operon structure of mutY/yggX in *E. coli* and *S. enterica* LT2. Promoters were mapped by Gifford and Wallace in *E. coli* (Gifford, C. M. and Wallace, S. S., *J. Bacteriol.* 181:4223-36,1999).

FIG. 2. Increased levels of YggX protein in yggX* mutant. Western blot analysis was preformed according to Harlow and Lane (Harlow, E. and Lane, D. (1988) *Antibodies* (Cold Spring Harbor Laboratory, USA). Proteins were visualized using alkaline phosphatase conjugated to anti-rabbit secondary antibody (Promega, Madison, Wis.). Lanes A, B and C were loaded with crude cell-free extracts (1 μg protein) from strains DM5104, DM5105 (yggX*) and DM5647 (yggX::Gm), respectively. Lane D was loaded with 1 ng purified YggX.

FIG. 3. The yggX* mutation does not increase MNNG resistance of gshA mutants. Strain LT2 was grown in LB with (▼) and without (Δ) 60 μM MNNG. Both gshA (○) and gshA yggX* (●) mutant strains were grown in LB with 60 μM MNNG.

FIG. 4. The yggX* mutation increases resistance of *S. enterica* to PQ. Panel A shows growth of gshA (○) and gshA yggX* (●) mutant strains in LB with 4 μM PQ.

Panel B shows growth of LT2 (Δ) and yggX* (▼) strains in LB with 40 μM PQ.

FIG. 5. yggX* does not require soxR to mediate resistance to PQ. Strains LT2 (♦), soxR (◇) and soxR yggX* (▲) were grown in LB with 4.0 μM PQ.

FIG. 6. Model showing how YggX protects *S. enterica* from oxidative damage. The result of superoxide attack on [Fe—S] clusters is depicted. We hypothesize that YggX is able to block oxidative damage to labile clusters and thus prevents the normal downstream consequences of such oxidation.

DETAILED DESCRIPTION OF THE INVENTION

In brief, the present invention involves the use of YggX, a protein identified from *Salmonella enterica* Serovar Typhimurium, or the homolog of this protein to protect cells or oxygen-labile enzyme from oxidated damage. By "homolog" we mean a protein with a function substantially identical to the Salmonella typhimurium YggX protein with at least a 45%, preferably 55%, amino acid identity. FIG. 1A compares the YggX homologs of various bacterial species. Of the 17 invariable amino acids, a homolog suitable for the present invention will comprise at least 14 and preferably all 17. We have compared a number of sequences and have found that 14 of the residues are invariant throughout all sequences examined. The conserved motif of suitable homologs is MXRXXXCXXX XXXXXXXXXX XXPXXXGXXX XXXXXXXXWX XWXXXQTXLX NEXXLXXXXX XXRXX (SEQ ID NO: 1), wherein X is any amino acid.

These 14 residues are represented by dark shading in FIG. 1A. A preferred sequence of the present invention will comprise these 14 invariant residues and will be approximately the same size as the YggX protein.

In one aspect of the present invention, one would overexpress the YggX protein or its homolog in a cell to provide resistance to superoxide damage. (By "overexpress", we mean that the protein will be expressed at greater than native levels.) One would preferably first amplify the YggX gene from the bacterial chromosome and ligate the gene into a standard expression vector suitable for the strain to be protected. One would use the expression of the YggX gene and, preferably, examine the strain to determine resistance to oxidative damage.

Resistance to oxidative damage would preferably be determined by the ability of the cell to grow in an increased concentration of super oxide producing compounds (e.g. paraquat) compared to the cell with lower levels of YggX protein.

In another embodiment of the present invention, one would co-express the YggX protein or its homolog with an oxygen-labile protein, preferably one with an iron sulfur cluster center. In this manner, one would protect the particular protein from superoxide damage. If one wished to co-express YggX to stabilize an oxygen-labile protein, one would first amplify the yggX gene from a bacterial chromosome that contains a homolog using standard PCR techniques. One would then ligate the yggX gene into a standard expression vector and transform the yggX expression vector into a strain that can express the oxygen-labile protein of interest. When inducing the strain to express the protein of interest, one would also induce expression of the yggX gene. The "stabilization" of oxygen-labile proteins would preferably be measured by detecting increased activity of an oxygen-labile protein or by recovering increased yield of the active protein. Preferred oxygen-labile proteins are those containing at least one [FE] cluster.

While we have performed experiments thus far in bacterial cells we anticipate a similar mechanism of protection to occur with YggX in other cell types, including yeast, mammalian and plant cells. This expectation is due to the similarity of structure, function and oxygen lability of [Fe—S]-containing proteins in each of these cell types.

One could obtain the YggX protein through standard molecular biology techniques and reference to Gralnick and Downs, *Proc. Natl. Acad. Sci.* 98(14):8030-8035, 2001, incorporated by reference. Applicants note that the amino acid sequence of the *E.Coli* YggX is listed at GenBank accession number AAC75999 (SEQ ID NO:11).

In another aspect of the present invention, one would use the YggX protein or its homologs as the target for antibiotics. In one embodiment, one would examine test compounds to determine whether the compound affected the activity of the YggX protein. Successful compounds would make excellent candidates for antibiotics.

Successful compounds that affect the activity of YggX could be identified as those that reverse the growth advantage (i.e., increased resistance to paraquat) that is allowed by increased levels of YggX protein. One would develop an in vitro assay fro YggX, and these compounds would be expected to alter the kinetic parameters YggX in the assay.

EXAMPLES

We disclose herein that elevated levels of the YggX protein increase the resistance of *Salmonella enterica* to superoxide stress, reverse enzymatic defects attributed to oxidized [Fe—S] clusters, and decrease the spontaneous mutation frequency. The data are consistent with a model in which YggX protects protein [Fe—S] clusters from oxidation.

Materials and Methods

Strains, media and DNA manipulations. Strains used were derivatives of *S. enterica* Serovar Typhiumurium strain LT2. Media, antibiotics, and insertion nomenclature have been described previously (Gralnick, J., et al., *J. Bacteriol.* 182: 5180-7, 2000). All chemicals were purchased from Sigma Chemical Co.

Enzymes for DNA manipulations were purchased from Promega and used as per the manufacturer's instructions. Sequencing was carried out by the University of Wisconsin Biotechnology Center. PCR amplification of *S. enterica* yggX used *E. coli* ORFmers (b2962-A, b2962-C) with conditions specified by the manufacturer (Sigma-Genosys).

Genetics i) Transduction. The methods of transduction using P22 (HT105/1, int-201) (Schmieger, H., *Mol. Gen. Genet.* 119:75-88, 1972) and purification of transductants has been described (Downs, D. M., *J. Bacteriol.* 174:1515-21, 1992).

ii) Isolation of mutants overexpressing YggX (yggX*). Cells from an overnight nutrient broth (NB) culture were pelleted, washed twice with NaCl (85 mM), and aliquots plated on minimal glucose medium. Colonies arose after 2-3 days of 37° C. incubation. A Tn10d (Cm) insertion (Way, J. C., et al. *Gene* 32:369-79, 1984) linked to the causative mutation was identified by standard genetic techniques (Kleckner, N., et al. *J. Mol. Biol.* 1 16:125-59, 1977).

iii) Identification of yggX locus. Genomic DNA from a suppressed gshA strain was partially digested with Sau3A, ligated into vector pSU19(Cm), and the resulting DNAs were electroporated into LT2 cells. Electroporants were selected for $Cm^R$ and screened for increased resistance to paraquat PQ (100 µL 0.1% PQ spread on a NB plate). Plasmid DNA was isolated, electroporated into strains DM271 (apbE) and DM4620 (gshA) and prototrophy scored. One clone, pPQR4 (FIG. 1), satisfied all requirements, and was used further.

iv) Generation of chromosomal yggX insertion. Plasmid pYGGX3A::Gm was transduced into a polA-deficient strain (DM3961). The transduction was allowed to proceed for 1 hour, cells were then washed twice in LB+5 mM EGTA and incubated at room temperature overnight prior to spreading onto NB/Gm plates. Colonies that arose on NB/Gm plates were screened for $Cm^S$, indicating loss of the parent plasmid by a double crossover event. The $Gm^R$ cassette from $Gm^R Cm^S$ strains was transduced into wild type LT2; the insertion in yggX was confirmed by PCR amplification.

v) Strain construction. A soxR deletion strain of *Escherichia coli* (DJ901) was obtained and the marker (zjc-2204::Tn10 (Km)) linked to the deletion (Greenberg, J. T., et al., *Proc. Nat. Acad. Sci. USA* 87:6181-5,1990) was transduced into *S. enterica* LT2 via a mutS intermediate as described (O'Brien, K., et al., *Gene* 11813-9,1992; Beck, B. J., et al., *J. Bacteriol.* 179:6504-8,1997). Transductants were scored for the ΔsoxR901 allele (sensitivity to 4 µM paraquat, (PQ)). An isogenic pair of strains with (DM5317) and without (DM5319) the ΔsoxR901 allele was constructed. The presence of the yggX* mutation in relevant strains was confirmed by backcross into a gshA strain (DM4620).

vi) Nutritional requirements. Nutritional requirements were tested with solid medium, soft agar overlays and growth curves in micro-titer plates (Petersen, L., et al., *Genetics* 143:37-44, 1996; Christian, T. and Downs, D. M., *Can. J. Microbiol.* 45:565-72, 1999).

vii) Spontaneous mutation frequency. Cultures were grown by shaking overnight in LB at 37° C. Aliquots (100-200 µl) were plated on solid LB media containing 100 µg/ml rifampacin, and incubated overnight at 37° C. In the case of d-cycloserine resistance, cultures were grown overnight in defined medium. Aliquots (10-100 µl) were plated on minimal glucose plates containing 0.2 mM d-cycloserine (0.2 M stock in phosphate buffer pH 8.0), and incubated overnight at 37° C. Colony-forming units (CFUs) were determined by plating on non-selective media.

Enzyme assays. i) Aconitase. Aconitase activity was assayed in cell-free crude extracts by the protocol of Gruer and Guest (Gruer, M. J. and Guest, J. R., *Microbiology* 140:2531-41,1994), as modified by Skovran (Skovran, E. and Downs, D. M., *J. Bacteriol.* 182:3896-903, 2000). Specific activity was described in Units/mg protein where a unit was the change in absorbance at 240 nm per minute. Protein concentration was determined by the Bradford Assay (Bradford, M. M., *Anal. Biochem.* 72:248-54,1976).

ii) Superoxide Dismutase (EC 1.15.1.1). SOD assays were modified from McCord and Fridovich (McCord, J. M. and Fridovich, I., *J. Biol. Chem.* 244:6049-55, 1969). Cultures (5 mL of LB grown overnight at 37° C.) were washed once with 3 mL 50 mM $KH_2PO_4$/0.1 mM EDTA, then resuspended in 1 mL of this buffer. Cells were kept on ice and sonicated 3 times 10 seconds (0.5 second pulses, power set to 3) using a Sonic Dismembrator 550 (Fischer Scientific). Extracts were centrifuged to remove cell debris and unbroken cells, and kept on ice until assayed. A unit of SOD activity was as described (McCord, J. M. and Fridovich, I., supra, 1969).

YgqX overexpression and purification. The yggX gene was cloned into the NdeI and SmaI sites of the pTYB2 expression vector (New England Biolabs) contained in the IMPACT T7 Kit. The resulting plasmid, pJAG100, was electroporated into strain BL21 (γDE3). Overexpression and purification were performed per manufacturer's recommendations, with the exception that the dithiothreitol (DTT) concentration used during the on-column cleavage step was 50 mM. Protein was concentrated using an Ultrafree-15 centrifugal filter device (Millipore Corporation) with a 5K MW cutoff. Anti-YggX polyclonal rabbit antibodies against purified YggX were generated at the University of Wisconsin Animal Care Unit.

Results

A suppressor of gshA mutant phenotypes. We recently demonstrated that gshA mutants of *Salmonella typhimrium serovar Typhimurium* strain LT2 are thiamine auxotrophs (Gralnick, J., et al., supra, 2000). When a gshA mutant strain was incubated on minimal glucose plates for 2-3 days, colonies arose at a frequency of ~$10^{-5}$. Genetic analyses of 10 independent colonies demonstrated that prototrophic growth resulted from a single lesion. An insertion (zgf-8077::Tn10d(Cm)) was 80% linked by P22 transduction to the causative mutation in each of the 10 revertants. The suppressing allele was designated yggX*, to be consistent with annotation of the *E. coli* genome.

An intact yggX locus is required for suppression. A plasmid library was generated using genomic DNA from a gshA yggX* double-mutant strain (DM5015). Assuming the yggX* mutation was dominant, clones were screened for ability to confer PQ resistance (see below), and prototrophic growth to strain DM4620 (gshA). One such plasmid (pPQR4) is diagrammed in FIG. 1, and was further characterized. Sequence analysis determined that plasmid pPQR4 contained two full genes (yggx, mltC), and part of a third (mutY). Since additional independent clones also carried yggX, the involvement of this gene in prototrophic growth was pursued. A DNA fragment containing yggX and reduced flanking sequences was PCR-amplified from pPQR4 and used to generate plasmid pYGGX3A (FIG. 1). This plasmid conferred the same growth phenotype as pPQR4, establishing the sufficiency of the yggX gene for suppression.

To investigate the role of yggX in the growth phenotype, a targeted null mutation was generated. A cassette encoding gentamycin resistance (Schweizer, H. D., *Biotechniques* 15:831-4, 1993) was engineered into a unique Bg/II site in the yggX coding sequence on plasmid pYGGX3A. The resulting plasmid, pYGGX3A::Gm, failed to restore growth of strain DM4620 (gshA) on minimal glucose medium. When the chromosomal yggX::Gm insertion was transduced into strain DM5015 (yggX* gshA), the suppression of the thiamine requirement was lost. We concluded that an intact yggX locus was required for the phenotypic suppression caused by a yggX* mutation. No nutritional requirement was detected for the single yggX null mutant (data not shown).

Increased expression of yggX is sufficient for phenotypic suppression of gshA mutants. Three results led to the conclusion that the yggX* mutation results in increased levels of YggX protein that cause the phenotypes attributed to this mutation. First, there were no differences in the yggX coding sequence between wild-type and yggX* strains. Second, ORFmers were used to amplify the yggX coding sequence from wild-type and yggX* mutant strains and generate plasmids containing only the yggX coding region in each of two orientations. Only the two plasmids with inserts properly oriented with respect to the plasmid encoded lac promoter restored prototrophic growth of the gshA mutant.

Third, Western-blot analyses of cell-free extracts showed that strain DM5105 (yggX*) had increased levels of YggX protein (11 kDa) compared to the isogenic strain DM5104 (FIG. 2). In fact, YggX was not detectable in the wild-type strain by this assay. The above results demonstrated that increasing the levels of YggX was sufficient to cause the phenotypes associated with the yggX* mutation and they were consistent with the yggX* mutation affecting expression of yggX.

The yggX gene is located at minute 66 on the *E. coli* and *S. enterica* chromosomes. In a number of organisms, yggX is located adjacent to mutY (encoding adenine DNA glycosylase), and at least in *E. coli*, these genes appear to be co-transcribed (Gifford, C. M. and Wallace, S. S., *J. Bacteriol.* 181:4223-36, 1999). The gene organization of mutY and yggX appears to be conserved in at least 17 out of the 23 eubacteria. We have not found yggX sequences in any archeal or eukaryotic genome sequences available in the GenBank Database at NCBI.

Increased level of YqgX does not act by increasing the cellular levels of free thiols. Inactivation of gshA results in loss of GSH, the predominant free thiol in the cell (Apontoweil, P. and Berends, W., *Biochim. Biophys. Acta* 399:10-22, 1975). Since the phenotypes of a gshA mutant must be explained in the context of this loss, it was conceivable that the phenotypic suppression by yggX* could be due to either gshA-independent formation of GSH, or elevation of a distinct free-thiol pool. The results of two experiments eliminated both of these possibilities. First, GSH levels of 14.0 pmol/mg wet weight were detected in wild-type strain (LT2) using a glutathione cycling assay (Anderson, M. E., *Methods Enzymol.* 113:548-55, 1985), yet no GSH (<0.1 pmol) was detectable in either gshA or gshA yggX* mutant strains (DM5014 and 5015, respectively). Second, the yggX* mutation did not alter the sensitivity of a gshA mutant to N-methyl-N'-nitro-N-nitrosguanidine (MNNG). MNNG is a common mutagen whose toxicity is accelerated by the presence of free thiols in the cell (Lawley, P. D. and Thatcher, C. J., *Biochem. J.* 116:693-707,1970). Growth analyses were preformed in the presence of 60 μM MNNG and the results are presented in FIG. 3. As expected, strain DM5014 (gshA) was significantly more resistant to MNNG than wild-type strain LT2 (Kerklaan, P., et al., *Mutat. Res.* 122:257-66, 1983), and the yggX* mutation had no deleterious affect on this resistance. In fact the gshA yggx* double mutant (DM5015) appeared to have a slightly increased growth rate. A general stimulation of growth rate was obseryed in several strains containing the yggX* mutation or the overexpression plasmid, and was attributed to the general effect of increased levels of YggX on distinct areas of metabolism described below. The resistance of gshA yggX* double mutants to MNNG suggested that an increased level of YggX did not elevate the pool size of a free thiol.

The breadth of phenotypes suppressed by increased levels of YggX suggests a role for this protein in protecting [Fe—S] clusters. Mutants defective in gshA belong to a recently defined class of thiamine auxotrophs that share several phenotypic similarities (Gralnick, J., et al., supra, 2000; Skovran, E. and Downs, D. M., supra, 2000) including a requirement for the thiazole moiety of thiamine that can be eliminated by anaerobic growth. It has been proposed that this defect reflects an inability to repair the oxidized [Fe—S] cluster in the ThiH biosynthetic enzyme (Gralnick, J., et al., supra, 2000). Although the function of their gene products has not been determined, lesions in apbC (Petersen, L. A. and Downs, D. M., *J. Bacteriol.* 179:4894-900, 1997) and apbE (Beck, B. J. and Downs, D. M., *J. Bacteriol.* 180:885-91, 1998; Beck, B. J. and Downs, D. M., *J. Bacteriol.* 181:7285-90, 1999) result in a thiamine phenotype similar to that caused by a gshA mutation. The effect of the yggX* mutation on thiamine-independent growth in these mutant strains was quantified, and data from representative experiments are shown in Table 1. The data showed that the requirement for thiamine was eliminated by a yggX* mutation in a strain defective in gshA, apbC, or apbE (Table 1, lines 2-7). These results were consistent with thiamine synthesis in these mutant strains being disrupted by a similar mechanism.

TABLE 1 yggX* mutation eliminates thiamine requirement of gshA mutants

| | | | Growth rate, μ | |
|---|---|---|---|---|
| Line | Strain | Relevant genotype | Minimal | Min + Thi |
| 1 | LT2 | Wild type | 0.45 | 0.47 |
| 2 | DM5014 | gshA | 0.11 | 0.32 |
| 3 | DM5015 | gshA yggX* | 0.46 | 0.35 |
| 4 | DM5784 | apbE | 0.09 | 0.31 |
| 5 | DM5783 | apbE yggX* | 0.44 | 0.42 |
| 6 | DM1774 | apbC | 0.20 | 0.37 |
| 7 | DM1773 | apbC yggX* | 0.46 | 0.45 |

Specific growth rate was determined by using $\mu = \ln(X/X_0)/T$, where X is $Abs_{650}$ during the log portion of the growth curve and T is time. Numbers shown are representative of at least two experiments.

Mutations in the isc gene cluster of *S. enterica* (Skovan, E. and Downs, D. M., supra, 2000) and *E. coli* (Schwartz, C. J., et al., *Proc. Natl. Acad. Sci. USA* 97:9009-14, 2000; Lauhon, C. T. and Kambampati, R., *J. Biol. Chem.* 275: 20096-103, 2000) cause a number of metabolic phenotypes, two of which are relevant here. A polar mutation in iscA caused a requirement for thiazole similar to that described for the class of mutants discussed above (Skovan, E. and Downs, D. M., supra, 2000). This requirement was eliminated by the presence of either the yggX* mutation or plasmid pYGGX3A (data not shown). Further, the nicotinic acid requirement generated by lack of the iscS gene was eliminated by the overexpression of YggX (Skovan, E. and Downs, D. M., supra, 2000), unpublished results). The nicotinic acid requirement can be traced back to a reduced activity of NadA (quinolinic synthetase) (Skovan, E. and Downs, D. M., supra, 2000; Zhu, N. in Biology (Thesis, University of Utah, Salt Lake City, 1990, an enzyme that also contains an oxygen-labile [Fe—S] center (Gardner, P. R. and Fridovich, I., supra, 1991).

The emerging correlation between increased YggX levels and activity of [Fe—S] proteins prompted us to address aconitase activity. In both *E. coli* (Gardner, P. R. and Fridovich, I., supra, 1993) and *S. enterica* (Gralnick, J., et al., supra, 2000), gshA mutants have reduced total aconitase activity. This loss in activity was suggested to reflect an inability to repair the oxidized [Fe—S] center of Acn in the absence of GSH (Gardner, P. R. and Fridovich, I., supra, 1993). The specific activity of aconitase in cell-free extracts of wild-type, gshA and gshA yggX* mutant strains was 3.50±0.32, 1.23 ±0.22, and 3.66+0.23 Units/mg protein, respectively.

Increased levels of YggX restored activity of at least two enzymes when assayed nutritionally (ThiH, NadA) and one when assayed biochemically (Acn). The ability of the yggX* mutation to completely restore Acn activity makes it feasible that suppression of the nutritional requirements reflects a significant change in the relevant enzyme activities. Experiments below identified additional metabolic consequences of increased levels of YggX, all of which could be accounted for by a model in which YggX was either limiting oxidation of [Fe—S] centers and/or facilitating their repair.

Increased levels of YggX result in soxR-independent resistance to superoxide. Strains carrying the yggX* mutation, or the expression plasmids described above, displayed increased resistance to superoxide. Supplementing the growth medium with the redox-cyling herbicide paraquat (PQ) increased the concentration of superoxide (Hassan, H. M., *Methods Enzymol.* 105:523-32, 1984). FIG. 4 illustrates the effect of the yggX* mutation on the growth of four strains in the presence of PQ. Data in FIG. 4A show that wild-type *S. enterica* grew slowly in the presence of 40 lM PQ, and that a yggX* mutation restored rapid growth. A gshA mutant was sensitive to the presence of 4 μM PQ, as shown in FIG. 4B (Gralnick, J., et al., supra, 2000), and the yggx* mutation improved growth, restoring it to a wild-type rate. In other experiments using phenazine methosulfate (PZ, 16 μM) as the generator of superoxide, similar trends were seen. In a representative experiment, the specific growth rates of a gsha (DM5014) and a gshA yggX* mutant strain (DM5015) in LB containing PZ were 0.15 and 0.51, respectively.

Growth in PQ induces expression of genes in the soxRS regulon, currently the best understood system to combat superoxide stress (Liochev, S. I., et al., supra, 1999). To test if the increased resistance of the yggX* mutants to PQ was mediated through the soxRS regulon, various strains with lesions in soxR were constructed and analyzed. Some of the data from these experiments are shown in FIG. 5. In our system, as in others, a soxR mutant (DM5317) was more sensitive to PQ than the isogenic soxR⁺ strain (DM5319). The growth data showed that a yggX* mutation significantly increased the resistance of the soxR strain to PQ (0.4 μM), but was unable to restore resistance to the wild-type level. We observed that a yggX* mutation restored prototrophic growth to a gshA mutant strain, even in the presence of the soxR mutation (data not shown). Together, these results indicated that the resistance to PQ allowed by increased levels of YggX was not mediated through the soxRS system. Since inactivation of enzymes containing labile [Fe—S] centers contributes to the lethality of PQ, these results were also consistent with a model in which YggX protects [Fe—S] centers from oxidation.

It was formally possible that YggX overexpression increased the cellular level of SOD activity independent of the soxRS system. When SOD activity of the wild-type (DM5104) and yggX* mutant strain (DM5105) were measured to address this possibility, they were found to be 6.78±0.49 and 6.61±0.49 units, respectively.

Increased levels of YqqX result in a decreased frequency of spontaneous mutations. A role for YggX in mutagenesis was explored for two reasons. First, the conserved location of yggX adjacent to mutY raised the possibility that YggX was associated with MutY function. It was intriguing that MutY itself contains an [Fe—S] center, while it functions under conditions of oxidative stress in the repair of oxidatively damaged DNA (Boiteux, S. and Radicella, J. P., supra, 1999; Michaels, M. L., et al., supra, 1990; Michaels, M. L., et al., supra, 1992). In a more general context, our working model suggests that YggX reduces the oxidation of [Fe—S] clusters (see below). Thus, YggX would reduce the loss of Fe(II) ions from clusters. The resulting decrease in free-iron levels would generate fewer hydroxyl radicals and thus reduce DNA damage (Keyer, K. and Imlay, J. A., supra, 1996). As an initial test of this aspect of the model, the frequency of spontaneous mutants acquiring resistance to rifampicin or d-cycloserine was determined in several strains. Representative data for these two assays of mutation frequency are shown in Table 2. As shown by the data in Table 2, in an otherwise wild-type background, the yggX* mutation reduced the number of spontaneous mutations by greater than ten-fold. As predicted by our working model, a gshA mutant displayed an increased mutation frequency. When the yggX* mutation was present in the gshA mutant background, the frequency of Rf colonies was decreased from 176 to a background level of $1-2/10^8$. A similar trend was noted in the frequency of spontaneous mutants resistant to d-cycloserine.

Discussion

This work was initiated to characterize a frequent mutation that suppresses the requirement of a class of thiamine auxotrophs (Gralnick, J., et al., supra, 2000). Molecular analysis found the causative mutation, yggX*, increased the level of the YggX protein. Overexpression of the yggX gene was found to alter several metabolic processes "unrelated" to thiamine synthesis. The phenotypes resulting from YggX overexpression are broad enough to suggest a role for this protein in a central metabolic process. Our working model holds that YggX protects labile [Fe—S] clusters from attack by oxygen species, including superoxide.

FIG. 6 depicts the consequences of superoxide radicals relevant to our model for the function of YggX. Superoxide (and/or other oxygen species) attack the labile [Fe—S] centers in a number of proteins (e.g., aconitase) (Flint, D. H., et al., supra, 1993; Gardner, P. R. and Fridovich, I., supra, 1991; Gardner, P. R. and Fridovich, I., supra, 1991; Gardner, P. R. and Fridovich, I., supra, 1992; Flint, D. H., et al., *J. Biol. Chem.* 268:14732-42. 1993). This molecular attack results in inactivation of the respective enzymes, and release of both free-iron and hydrogen peroxide that generates DNA damaging hydroxyl radicals via Fenton chemistry (Keyer, K. and Imlay, J. A., supra, 1996; Liochev, S. I . and Fridovich, I., supra, 1994; Srinivasan, C., et al., supra, 2000). It was suggested that in a wild-type cell, glutathione minimizes the effects of oxidation damage by providing reductant to facilitate reconstitution of the [Fe—S] clusters (Gardner, P. R. and Fridovich, I., supra, 1993), completing a cycle of damage and repair to the [Fe—S] clusters that remains in equilibrium under normal growth conditions. When GSH is absent (e.g., a gshA mutant), the effects of these oxygen species are exacerbated and the resulting phenotypes include, reduced activity of enzymes with labile [Fe—S] centers (i.e., ThiH, Acn), increased sensitivity to the superoxide (e.g., growth in PQ), and increased mutation frequency. Increasing the level of YggX reversed each of these phenotypes. One interpretation of these results is that YggX acts prior to the damage and protects labile [Fe—S] clusters from oxidation. In this scenario, blocking the initial attack on the [Fe—S] clusters would abrogate the above phenotypes (FIG. 6). It is formally possible the YggX acts to remove superoxide or to facilitate GSH independent repair of the oxidized clusters. We observed no increased superoxide dismutase activity in yggX* mutant extracts, and elevated levels of YggX increased the resistance of a wild-type strain (i.e., not limited for GSH) to superoxide suggesting that cluster repair is not the affected step.

This work and the model described above are consistent with the suggestion that the requirement of gshA mutants for the thiazole moiety of thiamine was due to the oxygen lability of the ThiH enzyme (Gralnick, J., et al., supra, 2000). The recent identification of ThiH as a member of a SAM radical protein family is consistent with this notion since members of this family share a motif that is indicative of an oxygen labile [Fe—S] cluster (Sofia, H. J., et al., *Nucleic Acids Res.* 29:1097-106, 2001; Frey, P. A. and Booker, S., *Advances in Free Radical Chem.* 2:1-43, 1999). Thus, the characterization of YggX presented here supports our hypothesis that the role of GSH in thiamine synthesis is in repair of the oxidized [Fe—S] cluster in ThiH (Gralnick, J., et al., supra, 2000).

This work raises a number of provocative questions for future studies. The phenotypes characterized here were the result of relatively high levels of YggX. The conserved location of yggx adjacent to mutY is intriguing. MutY contains an [Fe—S] center and must function under conditions of oxidative stress to perform its role in repairing oxidatively damaged DNA. Considering results herein, we suggest that YggX protects the [Fe—S] cluster of MutY under conditions of oxidative stress. Although in vitro studies on the homolgous enzyme Endonuclease III suggest the [Fe—S] cluster in MutY is not accessible to oxidation (Cunningham, R. P., et al., *Biochemistry* 28:4450-5, 1989), the need for protection in vivo or perhaps during protein folding following synthesis, maturation, and/or conformation changes associated with function are not ruled out.

The model proposed for the function of YggX in vivo encourages us to develop an in vitro assay for protection of oxygen labile [Fe—S] clusters. Such in vitro experiments may distinguish between various mechanisms that could explain the in vivo results and also help frame questions to dissect the possible connection between MutY and YggX functions.

In summary, our work has provided insight on the function of a previously uncharacterized ORF in *S.enterica*. By the serendipitous use of a strain that was sensitive to the lack of GSH we were able to identify a phenotype associated with increased cellular levels of YggX and offer a plausible model for the role of YggX in cellular metabolism.

We claim:

1. A method of reducing superoxide damage to a bacterial cell, comprising the steps of
   a. vector-based expression of a nucleic acid encoding the YggX polypeptide as set forth in SEQ ID NO:11, wherein the vector-based expression is in the bacterial cell, wherein the cells are rendered more resistant to superoxide damage relative to cells lacking endogenous YggX gene expression, wherein the cells comprise an oxygen-labile enzyme comprising an Fe—S cluster, and wherein there is no increased superoxide dismutase activity in the cells, and
   b. examining the oxygen-labile enzyme to determine the amount of oxidative damage.

2. A method of increasing the resistance of a bacterial enzyme having an oxygen labile Fe—S cluster/center to oxidative damage, comprising
   a. co-expressing the enzyme with a vector-based expression of a nucleic acid encoding the YggX polypeptide as set forth in SEQ ID NO:11, wherein the vector-based expression is in a bacterial cell, wherein the cells are rendered more resistant to superoxide damage relative to cells lacking endogenous YggX gene expression, and wherein there is no increased superoxide dismutase activity in the cells, and
   b. examining the oxygen-labile enzyme to determine the amount of oxidative damage.

* * * * *